United States Patent [19]

Danilewicz

[11] Patent Number: 5,798,352

[45] Date of Patent: Aug. 25, 1998

[54] ANTITHROMBOTIC AMIDINOTETRAHYDROPYRIDYLALANINE DERIVATIVES

[75] Inventor: John Christopher Danilewicz, Sandwich, United Kingdom

[73] Assignee: Pfizer Inc., New York, N.Y.

[21] Appl. No.: 930,596

[22] PCT Filed: Apr. 1, 1996

[86] PCT No.: PCT/EP96/01459

§ 371 Date: Oct. 9, 1997

§ 102(e) Date: Oct. 9, 1997

[87] PCT Pub. No.: WO96/33993

PCT Pub. Date: Oct. 31, 1996

[30] Foreign Application Priority Data

Apr. 28, 1995 [GB] United Kingdom ............... 9508622

[51] Int. Cl.⁶ ............... C07D 401/14; A61K 31/47; A61K 31/55
[52] U.S. Cl. ............... 514/213; 514/307; 540/594; 546/145
[58] Field of Search ............... 540/594; 546/145; 514/213, 307

[56] References Cited

FOREIGN PATENT DOCUMENTS

| 0008746 | 3/1980 | European Pat. Off. |
| 0623595 | 11/1994 | European Pat. Off. |
| 9208709 | 5/1992 | WIPO |

*Primary Examiner*—Zinna Northington Davis
*Attorney, Agent, or Firm*—Peter C. Richardson; Gregg C. Benson; Robert T. Ronau

[57] ABSTRACT

This invention is directed to compounds of formula (I),

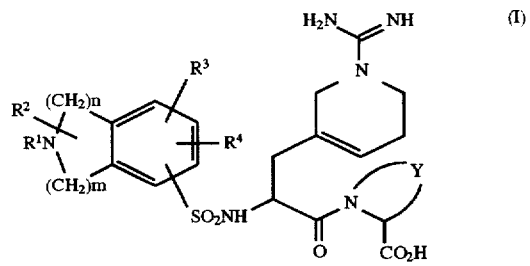

pharmaceutically acceptable salts thereof, and pharmaceutically acceptable solvates of either entity, wherein Y is optionally monounsaturated $C_3$–$C_5$ alkylene optionally substituted with $C_1$–$C_4$ alkyl or methylene; $R^1$ is H; $C_1$–$C_4$ alkyl optionally substituted with $C_1$–$C_4$ alkoxy, OH, $NR^5R^6$, $CONR^5R^6$, $C_3$–$C_6$ cycloalkyl or aryl; or $C_3$–$C_6$ alkenyl; $R^2$ is H; $C_1$–$C_4$ alkyl optionally substituted with $C_1$–$C_4$ alkoxy, OH, $NR^5R^6$, $CONR^5R^6$, $C_3$–$C_6$ cycloalkyl or aryl; or $CONR^5R^6$; $R^3$ and $R^4$ are each independently selected from H; $C_1$–$C_4$ alkyl optionally substituted with $NR^5R^6$; $C_1$–$C_4$ alkoxy; halo; $CONR^5R^6$ and aryl; aryl is phenyl optionally substituted with one, two or three substituents independently selected from $C_1$–$C_4$ alkyl, $C_1$–$C_4$ alkoxy, OH, halo and $CF_3$; $R^5$ and $R^6$ are each independently selected from H and $C_1$–$C_4$ alkyl; and m and n are each independently 1, 2 or 3; which are potent and selective thrombin inhibitors useful in the treatment of inter alia, deep vein thrombosis; reocclusion following thrombolytic therapy; chronic arterial obstruction; peripheral vascular disease; acute myocardial infarction; unstable angina; atrial fibrillation; thrombotic stroke; transient ischaemic attacks; restenosis and occlusion following angioplasty; or neurodegenerative disorders.

18 Claims, No Drawings

ANTITHROMBOTIC AMIDINOTETRAHYDROPYRIDYLALANINE DERIVATIVES

CROSS-REFERENCE TO RELATED APPLICATIONS

This invention is the national stage of international patent application number PCT/EP96/01459, filed Apr. 1, 1996, entitled "Antithrombotic Amidinotetrahydropyridylalanine Derivatives".

This invention relates to a series of amidinotetrahydropyridylalanine derivatives, which are antithrombotic agents, having utility in a variety of therapeutic areas including the prevention and/or treatment of deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); and restenosis and occlusion following angioplasty. They also have utility as an adjunct to thrombolytic therapy.

The compounds of the invention are potent and selective inhibitors of thrombin, which is the final serine protease enzyme in the coagulation cascade. The prime function of thrombin is the cleavage of fibrinogen to produce fibrin which forms linear insoluble polymers which, in turn, are cross-linked by factor XIIIa, itself activated by thrombin. In addition, thrombin regulates its own production by activation of factors V and VIII earlier in the cascade. It also has important actions at the cellular level, where it acts on specific receptors to cause platelet aggregation, endothelial cell activation and fibroblast proliferation. Thus thrombin has a central regulatory role in homeostasis and thrombus formation.

Clearly then, potent, selective and orally bioavailable thrombin inhibitors represent an attractive target for the convenient therapeutic control of thrombosis. In addition, thrombin potently causes neurite retraction and therefore a thrombin inhibitor is of potential therapeutic utility in the treatment of acute and chronic neurodegenerative disorders. Furthermore, the compounds disclosed herein are of potential value in the treatment of inflammatory disorders and scarring, and in wound healing.

Because of their potential as substrate mimics, arginine derivatives have been explored as thrombin inhibitors and this work led to the discovery of argatroban (see Cardiovascular Drug Rev., 1991, 9, 247). In turn, other research groups have sought to express the basic arginine function in a variety of alternative structures; for example, WO-A-92/08709 discloses amidino, guanidino, amidoximino, aminomethyl and amino phenylalanine derivatives as antithrombotic agents.

The compounds of the present invention are significantly more potent thrombin inhibitors than those mentioned above, selective (in comparison with their inhibition of, for example, trypsin, plasmin, butyrylcholinesterase and elastase), well tolerated and orally bioavailable.

Accordingly, the present invention provides a compound of formula (I):

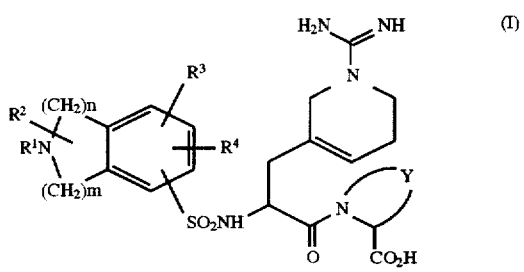

pharmaceutically acceptable salts thereof, and pharmaceutically acceptable solvates of either entity, wherein Y is optionally monounsaturated $C_3$–$C_5$ alkylene optionally substituted with $C_1$–$C_4$ alkyl or methylene;

$R^1$ is H; $C_1$–$C_4$ alkyl optionally substituted with $C_1$–$C_4$ alkoxy, OH, $NR^5R^6$, $CONR^5R^6$, $C_3$–$C_6$ cycloalkyl or aryl; or $C_3$–$C_6$ alkenyl;

$R^2$ is H; $C_1$–$C_4$ alkyl optionally substituted with $C_1$–$C_4$ alkoxy, OH, $NR^5R^6$, $CONR^5R^6$, $C_3$–$C_6$ cycloalkyl or aryl; or $CONR^5R^6$;

$R^3$ and $R^4$ are each independently selected from H; $C_1$–$C_4$ alkyl optionally substituted with $NR^5R^6$; $C_1$–$C_4$ alkoxy; halo; $CONR^5R^6$ and aryl;

$R^5$ and $R^6$ are each independently selected from H and $C_1$–$C_4$ alkyl; and m and n are each independently 1, 2 or 3.

In the above definition, aryl means phenyl optionally substituted with one, two or three substituents independently selected from $C_1$–$C_4$ alkyl, $C_1$–$C_4$ alkoxy, OH, halo and $CF_3$; halo means fluoro, chloro, bromo or iodo. Unless otherwise indicated, alkyl and alkoxy groups having three or more carbon atoms and alkenyl groups having four or more carbon atoms may be straight-chain or branched-chain.

The compounds of formula (I) contain two or more asymmetric centres and thus can exist as stereoisomers, i.e. as enantiomers or as diastereoisomers, and the invention includes both the separated individual stereoisomers as well as mixtures thereof.

The preferred stereoisomers are of formula (IA):

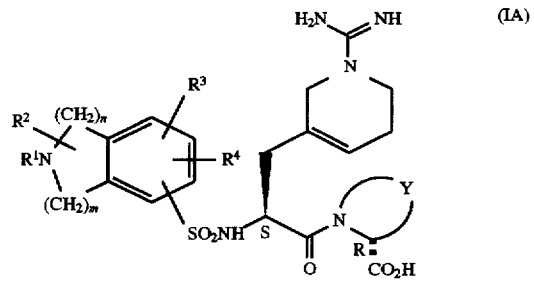

Also included in the invention are radiolabelled derivatives of compounds of formula (I) which are suitable for biological studies.

The pharmaceutically acceptable salts of the compounds of formula (I) are, for example, non-toxic acid addition salts formed with inorganic acids such as hydrochloric, hydrobromic, sulphuric and phosphoric acid, with organo-carboxylic acids, or with organo-sulphonic acids. Compounds of formula (I) can also provide pharmaceutically acceptable metal salts, in particular non-toxic alkali metal salts, with bases. Examples include the sodium and potassium salts.

A preferred group of compounds of formula (I) is that wherein Y is optionally monounsaturated $C_4$ alkylene substituted with methyl or ethyl; $R^1$ is $C_1$-$C_4$ alkyl; $R^2$ is H; $R^3$ and $R^4$ are H; and m and n are each independently 1 or 2.

A more preferred group of compounds is that of formula (IB):

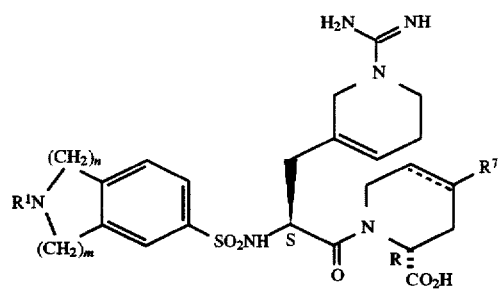

wherein —— represents an optional carbon-carbon single bond; $R^1$ and $R^7$ are methyl; m is 1 or 2; and n is 2.

Particularly preferred individual compounds of the invention include:

4-methyl-1-[N-(2-methyl-1,2,3,4-tetrahydroisoquinoline-7-sulphonyl)-3-(1-amidino-1,2,5,6-tetrahydro-3-pyridyl)-(S)-alanyl]-1,2,3,6-tetrahydropyridine-2(R)-carboxylic acid;

4-methyl-1-[N-(3-methyl-2,3,4,5-tetrahydro-1H-3-benzazepine-7-sulphonyl)-3-(1-amidino-1,2,5,6-tetrahydro-3-pyridyl)-(S)-alanyl]-1,2,3,6-tetrahydropyridine-2(R)-carboxylic acid; and 4(R)-methyl-1-[N-(2-methyl-1,2,3,4-tetrahydroisoquinoline-7-sulphonyl)-3-(1-amidino-1,2,5,6-tetrahydro-3-pyridyl)-(S)-alanyl]piperidine-2(R)-carboxylic acid;

and pharmaceutically acceptable salts thereof, and pharmaceutically acceptable solvates of either entity.

In another aspect, the present invention provides processes for the preparation of compounds of formula (I) and their pharmaceutically acceptable salts.

A compound of formula (I) may be prepared by hydrolysis of its lower alkyl ester precursor of formula (II):

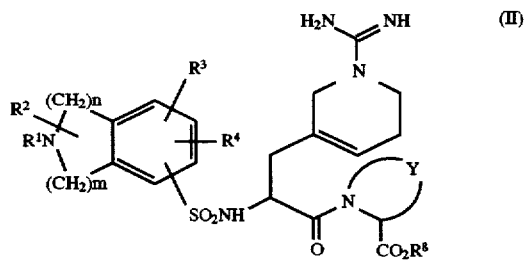

wherein $R^8$ is $C_1$-$C_3$ alkyl, preferably methyl or ethyl, and Y, $R^1$, $R^2$, $R^3$, $R^4$, m and n are as previously defined for formula (I). The reaction may be acid- or base-catalysed, but is generally carried out using an alkali metal hydroxide such as sodium or potassium hydroxide in aqueous solution, optionally in the presence of a suitable cosolvent, at from about 0° C. to about 100° C. Preferred conditions are the use of aqueous sodium hydroxide solution at from about 0° C. to about room temperature.

The novel intermediate esters of formula (II) also form part of the invention.

A compound of formula (II) may be prepared from a compound of formula (III):

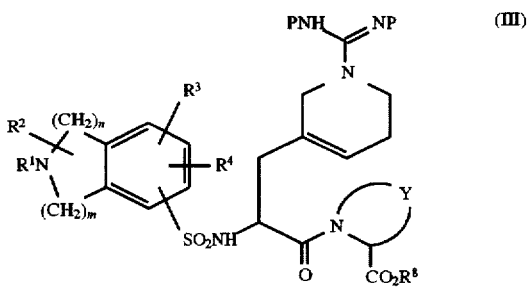

wherein P is a conventional amine protecting group and Y, $R^1$, $R^2$, $R^3$, $R^4$, $R^8$, m and n are as previously defined for formula (II). This may be achieved by double-deprotection of the protected amidine group under standard conditions. When P is the preferred protecting group, i.e. t-butoxycarbonyl (Boc), deprotection may be effected under acidic conditions, e.g. using trifluoroacetic acid or hydrogen chloride in a suitable solvent. Preferably the reaction is conducted using hydrogen chloride in dichloromethane at from about 0° C. to about room temperature.

A compound of formula (III) may be prepared by N-alkylation of a compound of formula (IV):

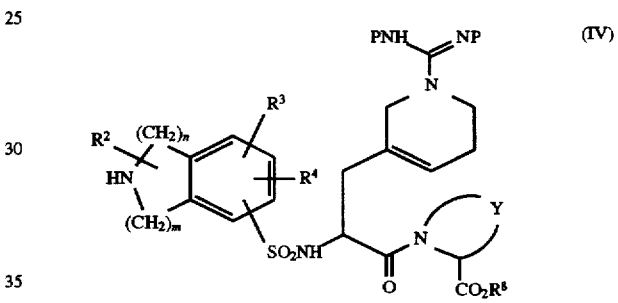

wherein P, Y, $R^2$, $R^3$, $R^4$, $R^8$, m and n are as previously defined for formula (III), with the proviso that none of the other nucleophilic centres within (IV) provides a more reactive alkylation site, e.g. in certain cases where $R^2$, $R^3$ or $R^4$ is $C_1$-$C_4$ alkyl substituted with $NR^5R^6$.

In general, the alkylation may be achieved by reaction of a compound of formula (IV) with a compound of formula $R^1Q$, wherein $R^1$ is as previously defined for formula (III) and Q is a suitable leaving group, e.g. halo, $C_1$-$C_4$ alkanesulphonyloxy, trifluoromethanesulphonyloxy or arylsulphonyloxy (such as benzenesulphonyloxy or p-toluenesulphonyloxy), in the presence of an appropriate base, e.g. the carbonate or bicarbonate salt of an alkali or alkaline earth metal, in a suitable solvent such as a $C_1$-$C_3$ alkanol, acetonitrile, dimethylformamide or N,N-dimethylacetamide, optionally in the presence of the iodide salt of sodium or potassium, at from about room temperature to about 100° C. Preferably Q is chloro, bromo or iodo, the base is sodium or potassium carbonate or bicarbonate, the solvent is acetonitrile and the reaction is conducted at about 80°–85° C.

When $R^1$ is methyl, the N-methylation can be conveniently carried out by a reductive alkylation procedure wherein (IV) is treated with aqueous formaldehyde solution followed by an appropriate reducing agent in a suitable solvent. Preferably both reaction steps are conducted at room temperature in dichloromethane as solvent, with sodium triacetoxyborohydride being employed in the reduction step.

A compound of formula (IV) may be prepared by N-deprotection of a compound of formula (V):

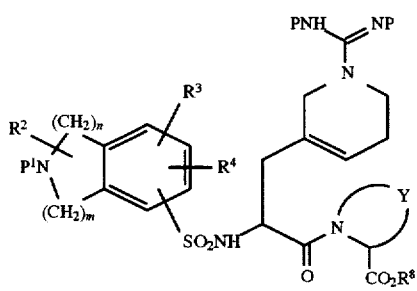

wherein $P^1$ is a protecting group and P, Y, $R^2$, $R^3$, $R^4$, $R^8$, m and n are as previously defined for formula (IV). $P^1$, which represents a conventional amine protecting group, is chosen with due regard to its compatibility with the various reagents employed in earlier synthetic steps of the over-all process and also to the reaction conditions required for its selective removal; preferably, it is trifluoroacetyl. The particular protecting group can be removed under standard conditions which, in the case of trifluoroacetyl, are mild aqueous base optionally in the presence of a $C_1$-$C_3$ alkanol as cosolvent. Preferred conditions are sodium or potassium carbonate in aqueous methanol or ethanol at about room temperature.

A compound of formula (V) may be prepared from a compound of formula (VI):

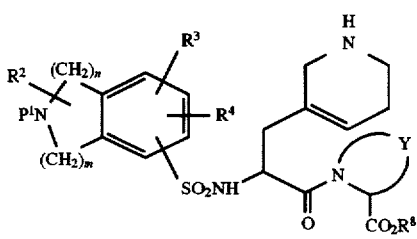

wherein $P^1$, Y, $R^2$, $R^3$, $R^4$, $R^8$, m and n are as previously defined for formula (V), by reaction with a S-alkylisothiourea derivative of formula (VII):

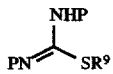

wherein $R^9$ is $C_1$-$C_3$ alkyl and P is as previously defined for formula (V), in a suitable solvent, optionally in the presence of a mercury(II) salt, at from about 0° C. to about room temperature.

A compound of formula (VI) may be prepared from a compound of formula (VIII):

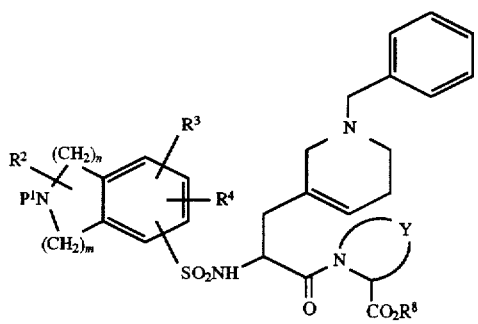

wherein $P^1$, Y, $R^2$, $R^3$, $R^4$, $R^8$, m and n are as previously defined for formula (VI), using a standard N-dealkylation reagent. In a preferred procedure, the debenzylation is effected by, in a first step, reaction of (VIII) with 1-chloroethyl chloroformate, optionally in the presence of 1,8-bis(dimethylamino)naphthalene, in a suitable solvent such as dichloromethane, 1,2-dichloroethane or toluene, at from about 0° C. to about 110° C., followed by a second step in which the intermediate carbamate is heated under reflux with a $C_1$-$C_3$ alkanol. Preferably, in the first step the solvent is dichloromethane and the reaction temperature is at from about 0° C. to about room temperature, while in the second step the alkanol is methanol or ethanol.

A compound of formula (VIII) may be assembled by a number of strategies. One approach may involve the coupling of a compound of formula (IX):

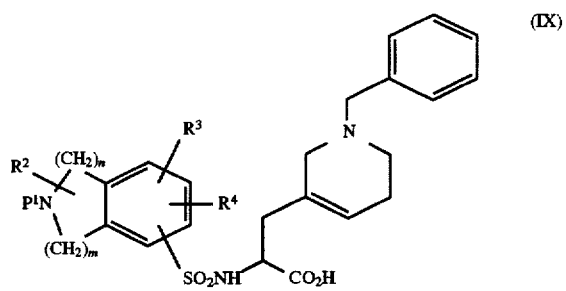

wherein $P^1$, $R^2$, $R^3$, $R^4$, m and n are as previously defined for formula (VIII), with a compound of formula (X):

wherein Y and $R^8$ are as previously defined for formula (VIII). The coupling reaction may be achieved using conventional amide bond-forming techniques. For example, the acid may be activated by formation of the corresponding acyl halide, e.g. bromide or chloride, followed by reaction of the latter with an amine of formula (X), optionally in the presence of a reaction-inert base to act as acid scavenger, in a suitable solvent such as dichloromethane. Alternatively, any of a host of peptide coupling variations may be used. For example, the acid may be activated using a carbodiimide such as 1,3-dicyclohexylcarbodiimide or 1-(3-dimethylaminopropyl)-3-ethylcarbodiimide, optionally in the presence of 1-hydroxybenzotriazole and, where appropriate, a reaction-inert amine such as N-methylmorpholine or N-ethyldiisopropylamine (for example when either (X) or the carbodiimide is in the form of an acid addition salt) and/or a catalyst such as 4-dimethylaminopyridine, in a suitable solvent such as dichloromethane. Thus, in a preferred process, (IX) is converted to the corresponding acyl chloride using oxalyl chloride and a catalytic amount of dimethylformamide in a suitable solvent, e.g. dichloromethane, at about 0°–5° C. and then the acyl chloride is reacted with (X), optionally as a suitable acid addition salt, in the presence of N-ethyldiisopropylamine as reaction-inert base in dichloromethane at from about 0° C. to about room temperature.

A compound of formula (IX) may be prepared from a corresponding ester of formula (XI):

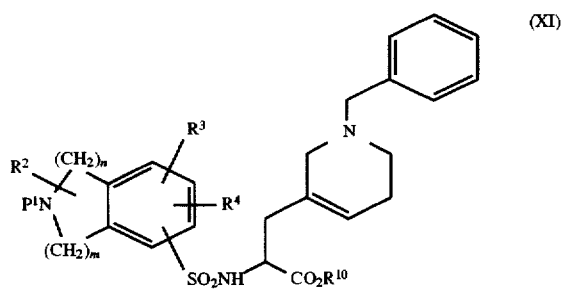

(XI)

wherein $R^{10}$ is $C_1$–$C_4$ alkyl or benzyl, and $P^1$, $R^2$, $R^3$, $R^4$, m and n are as previously defined for formula (IX). Preferably $R^{10}$ is t-butyl.

The conversion of (XI) to (IX) can be effected by standard hydrolytic or O-dealkylation procedures and will be dependent on the nature of $P^1$. For example, when $R^{10}$ is t-butyl and $P^1$ is trifluoroacetyl, protonolysis using a reagent such as trifluoroacetic acid or hydrogen chloride in a suitable solvent is the method of choice. Preferably the reaction is conducted using hydrogen chloride in dichloromethane at from about 0° C. to about room temperature.

A compound of formula (XI) may be prepared by sulphonylation of a compound of formula (XII):

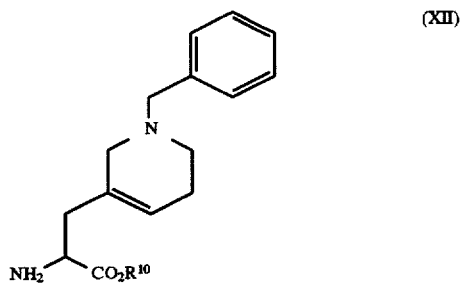

(XII)

wherein $R^{10}$ is as previously defined for formula (XI), optionally as a suitable acid addition salt, with a compound of formula (XIII):

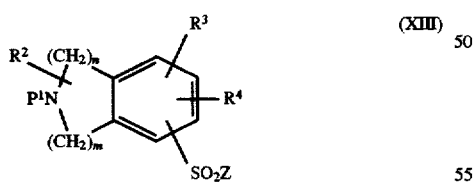

(XIII)

wherein Z is halo, preferably chloro, and $P^1$, $R^2$, $R^3$, $R^4$, m and n are as previously defined for formula (XI), under conventional conditions in the presence of a reaction-inert base in a suitable solvent at from about 0° C. to about room temperature. Preferably the base is N-ethyldiisopropylamine and the solvent is dichloromethane.

A compound of formula (XII) may be prepared by N-deprotection of a compound of formula (XIV):

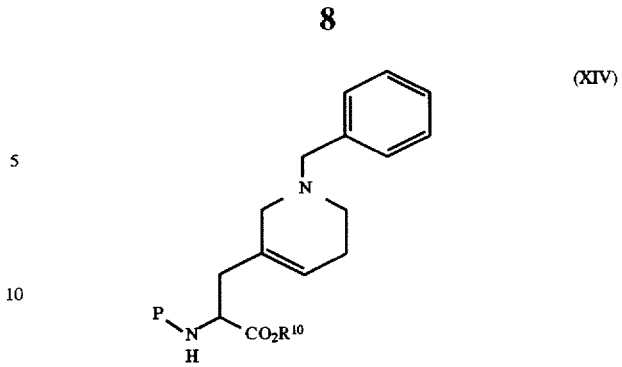

(XIV)

wherein $R^{10}$ is as previously defined for formula (XII) and P is as previously defined for formula (VII). As for a compound of formula (III), P is preferably Boc and (XIV) may be similarly deprotected. However, when $R^{10}$ is the preferred group (t-butyl), the deprotection method of choice involves the use of neat formic acid at about room temperature.

A compound of formula (XIV) may be prepared by partial reduction of a compound of formula (XV):

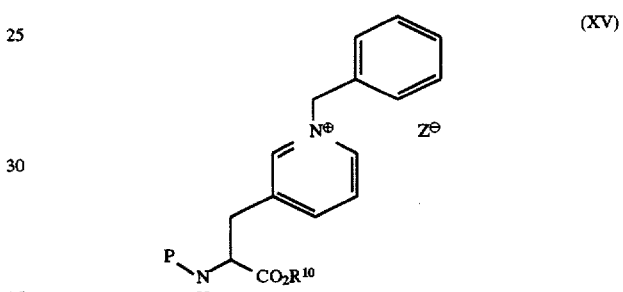

(XV)

wherein P and $R^{10}$ are as previously defined for formula (XIV) and Z is as previously defined for formula (XIII) but is preferably bromo, using a conventional reducing agent in a $C_1$–$C_3$ alkanol. A preferred method employs sodium borohydride in ethanol at about 0° C.

A compound of formula (XV) may be prepared by N-benzylation of a compound of formula (XVI):

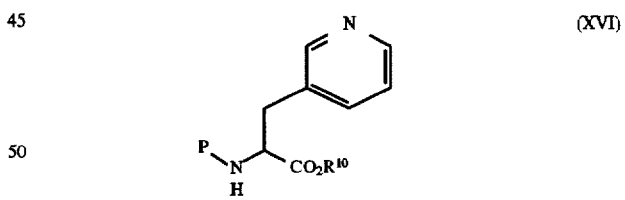

(XVI)

wherein P and $R^{10}$ are as previously defined for formula (XV), using the appropriate benzyl halide in a suitable solvent under standard conditions, e.g. benzyl bromide in ethanol at about room temperature.

The N-protected α-amino ester of formula (XVI) is obtainable from the corresponding α-amino acid, 3-(3-pyridyl)alanine (see Int. J. Pept. Prot. Res., 1987, 29, 118 for S- and R-enantiomers), using conventional amino acid protecting group chemistry. This may be achieved, for example, by effecting N-protection initially, followed by esterification of the carboxyl group using the appropriate alcohol of formula $R^{10}OH$.

A compound of formula (XIII) may be prepared from a compound of formula (XVII):

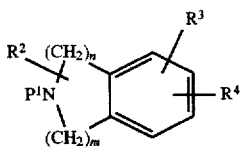 (XVII)

wherein $P^1$, $R^2$, $R^3$, $R^4$, m and n are as previously defined for formula (XIII), by the application of known methods for the electrophilic introduction of a $SO_2Z$ group, wherein Z is as previously defined for formula (XIII), into an aromatic ring system. For example, when Z is chloro, by the action of chlorosulphonic acid at from about $-15°$ C. to about room temperature.

A compound of formula (XVII) may be prepared from a compound of formula (XVIII):

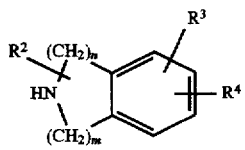 (XVIII)

wherein $R^2$, $R^3$, $R^4$, m and n are as previously defined for formula (XVII), by conventional procedures. For example, when $P^1$ is trifluoroacetyl, by using trifluoroacetic anhydride, optionally in the presence of a base such as N-methylmorpholine or N-ethyldiisopropylamine and a solvent such as dichloromethane at from about $0°$ C. to about room temperature.

A compound of formula (X) may be prepared by a variety of methods, e.g. by standard cyclic α-amino acid/ester syntheses, and, when a particular stereoisomer is required, by classical resolution procedures or by asymmetric synthesis.

For example, when (X) represents a compound of formula (XA):

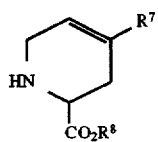 (XA)

wherein $R^7$ is as previously defined for formula (IB) and $R^8$ is as previously defined for formula (X), 4-methylpyridine offers a convenient starting point and may be processed as follows. Following quarternisation by alkylation, e.g. using a conventional methylation procedure, the resulting pyridinium salt is subjected to partial reduction using sodium borohydride followed by in situ α-cyanation of the 2,5-dihydropyridine intermediate using hydrogen cyanide to afford, in this example, 1-methyl-2(R,S)-cyano-4-methyl-1, 2,3,6-tetrahydropyridine. Next, the nitrile is converted to the required ester derivative and N-demethylation effected using a suitable chloroformate, e.g. 2,2,2-trichloroethyl chloroformate. Finally, N-deprotection is carried out using the appropriate reagent, e.g. zinc dust in this example.

An alternative approach to a compound of formula (XA) involves aza Diels-Alder cycloaddition chemistry in which an imine of formula (XIX), wherein $P^2$ is a suitable protecting group, e.g. benzyl, is reacted with a diene of formula (XX):

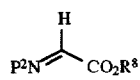 (XIX)

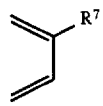 (XX)

(see Tetrahedron:Asymmetry, 1991,2,1263), followed by N-debenzylation, again using a chloroformate reagent, e.g. 1-chloroethyl chloroformate in this case. The final N-deprotection may be achieved using excess alcohol ($R^8OH$) at about reflux temperature.

Clearly, reduction of (XA), e.g. by catalytic hydrogenation, will provide the corresponding piperidine-2-carboxylic esters.

When $P^2$ also acts as a chiral auxiliary, e.g. it is 1(R)- or 1(S)-phenylethyl, a useful degree of asymmetric induction is achievable in the (4+2) cycloaddition reaction affording a mixture of easily separable diastereoisomers; the 1(S)-auxiliary induces (R)-stereochemistry at the 2-position and the 1(R)-auxiliary provides the antipodal series (see Tetrahedron:Asymmetry, 1991, 2,1263 and Tetrahedron, 1992,48,9707). N-Deprotection may be effected as above for the case wherein $P^2$ is benzyl, thus providing either the preferred 2(R)- or the 2(S)-enantiomer of (XA) respectively.

Again, catalytic hydrogenation of these enantiomers should lead to the (2R,4S)- and (2S,4R)-piperidine enantiomers respectively.

Alternative approaches to these piperidine enantiomers wherein $R^7$ is methyl, and also to the corresponding (2R, 4R)- and (2S,4S)-enantiomers, are described in Biochem.Biophys.Res.Comm., 1981,101,440, in which classical fractional distillation, fractional crystallisation of salts formed from optically active acids (L- and D-tartaric acid) and epimerisation techniques are employed.

Resolution may also be achieved by chromatographic separation procedures. For example, acid-catalysed hydrolysis of the cycloadduct formed from (XIX) wherein $P^2$ is benzyl, and (XX), affords 1-benzyl-4-methyl-1,2,3,6-tetrahydropyridine-2(R,S)-carboxylic acid which is then esterified under standard conditions with a chiral alcohol, e.g. a N-protected ephedrine derivative such as N-acetyl-(1R,2S)-ephedrine. N-Deprotection using, for example, 2,2, 2-trichloroethyl chloroformate followed by zinc dust as described above, followed by chromatography on silica gel, furnishes the individual 2(R)- and 2(S)-diastereoisomeric esters, each of which is processed as followed. N-Reprotection, e.g. using a Boc group, removal of the chiral auxiliary by base-catalysed hydrolysis, reesterification with $R^8OH$, and removal of the Boc group, provides the 2(R)- and 2(S)-enantiomers of (XA) whose identities can be confirmed by comparison with the enantiomers obtained by the asymmetric aza Diels-Alder chemistry previously described.

An alternative approach for assembling a compound of formula (VIII) may involve the sulphonylation of a compound of formula (XXI):

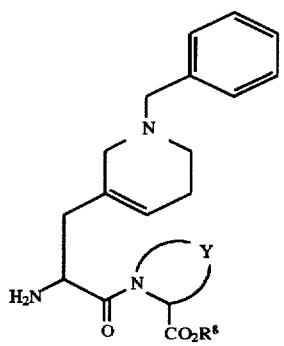

(XXI)

wherein Y and R⁸ are as previously defined for formula (VIII), with a compound of formula (XIII), under the conditions employed for reacting (XIII) with (XII).

A compound of formula (XXI) may be prepared from a compound of formula (XXII):

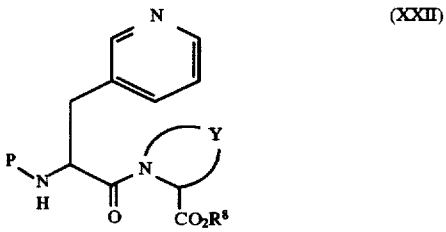

(XXII)

wherein P is as previously defined for formula (XVI) and Y and R⁸ are as previously defined for formula (XXI), by analogy with the reactions involved in the conversion of (XVI) to (XIV), followed by N-deprotection as already described for the conversion of (III) to (II).

A compound of formula (XXII) may be prepared by coupling the appropriately N-protected 3-(3-pyridyl)alanine with a compound of formula (X), using the conditions already described for coupling (X) with (IX). In a preferred process, the reagents employed are 1-(3-dimethylaminopropyl)-3-ethylcarbodiimide, 1-hydroxybenzotriazole and N-methylmorpholine, in dichloromethane as solvent, at from about 0° C. to about room temperature.

The bicyclic amines of formula (XVIII) and intermediates employed in the preparation thereof, when neither commercially available nor subsequently described, can be obtained either by analogy with the processes described in the Preparations section or by conventional synthetic procedures, in accordance with standard textbooks on organic chemistry or literature precedent, from readily accessible starting materials using appropriate reagents and reaction conditions.

Moreover, persons skilled in the art will be aware of variations of, and alternatives to, those processes described hereinafter in the Examples and Preparations sections which allow the compounds defined by formula (I) to be obtained.

The pharmaceutically acceptable acid addition salts of the compounds of formula (I) may also be prepared in a conventional manner. For example a solution of the free base is treated with the appropriate acid, either neat or in a suitable solvent, and the resulting salt isolated either by filtration or by evaporation under vacuum of the reaction solvent. Pharmaceutically acceptable base addition salts can be obtained in an analogous manner by treating a solution of a compound of formula (I) with the appropriate base. Both types of salt may be formed or interconverted using ion-exchange resin techniques.

The biological activities of the compounds of the present invention were determined by the following test methods.

Chromogenic Assays

The inhibition of thrombin, trypsin, plasmin or factor Xa is measured in 96 well plate chromogenic assays. The percentage inhibition and $IC_{50}$ are calculated from triplicate samples of an 8 concentration dose-response curve. From the substrate Km and $IC_{50}$, the Ki for each inhibitor is calculated. All assays are carried out in a total incubation of 200 μl of 50 mM HEPES and 150 mM NaCl at pH 8.0, and all compound dilutions are preincubated with enzyme at room temperature for 15 minutes prior to addition of substrate. After 30 minutes incubation at 30° C., the O.D. is measured at 405 nM in a 96 well plate reader. Thrombin activity is measured using bovine thrombin and S2238 (H-D-Phe-Pip-Arg-pNA), bovine pancreatic trypsin is assayed with S2222 (Benz-Isoleu-Glu-Gly-Arg-pNA), bovine plasma plasmin is assayed with Chromozym PL (Tosyl-Gly-Pro-Lys-pNA) and bovine fac or Xa is assayed in 50 mM Tris, 150 mM NaCl, pH 7.5 buffer with S2222.

Clotting Assays

Thrombin time (TT) and activated partial thromboplastin time (APTT) are measured using Instrumentation Laboratories (IL) Test TT reagent and IL Test APTT (ellagic acid) reagent respectively in an Automated Coagulation Laboratory (ACL), according to the manufacturer's instructions.

In Vitro

To 1 ml aliquots of rat pooled plasma (citrated), a ¹/₁₀₀ volume of a range of compound concentrations is added and preincubated at room temperature for 15 minutes, after which the TT and APTT are measured.

Ex Vivo

Compounds are dosed per os, intravenously or intraduodenally to rats. Pre- and post-dose blood samples are taken into citrate solution and plasma prepared. TT and APTT are measured as for in vitro assays.

In therapy, the compounds of formula (I), their pharmaceutically acceptable salts, and pharmaceutically acceptable solvates of either entity, can be administered alone, but will generally be administered in admixture with a pharmaceutical carrier selected with regard to the intended route of administration and standard pharmaceutical practice. Preferably, they are administered orally in the form of tablets containing such excipients as starch or lactose, or in capsules or ovules either alone or in admixture with excipients, or in the form of elixirs, solutions or suspensions containing flavouring or colouring agents. They can also be injected parenterally, for example intravenously, intramuscularly or subcutaneously. For parenteral administration, they are best used in the form of a sterile aqueous solution which may contain other substances, for example enough salts or glucose to make the solution isotonic with blood. For buccal or sublingual administration they may be administered in the form of tablets or lozenges which can be formulated in a conventional manner.

For oral, parenteral, buccal and sublingual administration to patients, the daily dosage level of the compounds of formula (I) and their pharmaceutically acceptable salts and solvates will be from 1 to 1000 mg (in single or divided doses). Thus tablets or capsules may contain from 0.5 to 500 mg of active compound for administration singly, or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited and such are within the scope of this invention.

Thus the invention provides a pharmaceutical composition comprising a compound of formula (I), or a pharmaceutically acceptable salt thereof, or a pharmaceutically acceptable solvate of either entity, together with a pharmaceutically acceptable diluent or carrier.

The invention also provides a compound of formula (I), or a pharmaceutically acceptable salt thereof, or a pharmaceutically acceptable solvate of either entity, or a pharmaceutical composition containing any of the foregoing, for use as a medicament.

The invention further includes the use of a compound of formula (I), or a pharmaceutically acceptable salt thereof, or a pharmaceutically acceptable solvate of either entity, or a pharmaceutical composition containing any of the foregoing, for the manufacture of a medicament for the curative or prophylactic treatment of deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); restenosis and occlusion following angioplasty; neurodegenerative disorders; inflammatory disorders; or scarring.

In a further aspect, the invention provides a method of treating a mammal (including a human being) to cure or prevent deep vein thrombosis (DVT) after surgery, major medical illness, paralysis, malignancy, prolonged immobilisation trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery bypass grafts); restenosis and occlusion following angioplasty; neurodegenerative disorders; inflammatory disorders; or scarring; which comprises treating said mammal with an effective amount of a compound of formula (I), or a pharmaceutically acceptable salt thereof, or a pharmaceutically acceptable solvate of either entity, or a pharmaceutical composition containing any of the foregoing.

The syntheses of the compounds of the invention and of the intermediates for use therein are illustrated by the following Examples and Preparations. The purity of the compounds (Rf) was routinely monitored by thin layer chromatography using Merck Kieselgel 60 $F_{254}$ plates and the following solvent systems (SS):

1. hexane:ether, 1:1;
2. ether;
3. dichloromethane:methanol:glacial acetic acid, 90:10:1;
4. hexane:ether, 4:1;
5. dichloromethane;
6. dichloromethane:methanol:0.880 aqueous ammonia, 95:5:0.5;
7. hexane:ethyl acetate, 3:7;
8. hexane:ethyl acetate, 1:1;
9. dichloromethane:methanol:0.880 aqueous ammonia, 90:10:1;
10. hexane:ethyl acetate, 3:1;
11. toluene:ethyl acetate, 4:1;
12. toluene:ethyl acetate, 1:1;
13. isobutyl methyl ketone:glacial acetic acid:water, 2:1:1 (upper phase);
14. ethyl acetate:ethanol, 4:1;
15. ethyl acetate:ethanol:glacial acetic acid, 90:10:0.4;
16. ethyl acetate:ethanol:glacial acetic acid, 80:20:1;
17. ethyl acetate:ethanol, 9:1;
18. hexane:ethyl acetate:diethylamine, 9:1:0.2;
19. hexane:ethyl acetate, 50:1;
20. dichloromethane:methanol, 97.5:2.5;
21. dichloromethane:ethanol, 97.5:2.5;
22. hexane:ethyl acetate, 1:4;
23. dichloromethane:methanol, 95:5;
24. dichloromethane:methanol:0.880 aqueous ammonia, 80:20:5;
25. dichloromethane:methanol:0.880 aqueous ammonia, 84:14:2;
26. ethyl acetate;
27. methanol:ethyl acetate:glacial acetic acid:0.880 aqueous ammonia:water, 60:12:4:4:8;
28. dichloromethane:methanol:0.880 aqueous ammonia, 95:5:1;
29. hexane:ethyl acetate, 1:2.

$^1$H Nuclear magnetic resonance (NMR) spectra were recorded using either a Nicolet QE-300 or a Bruker AC-300 spectrometer and were in all cases consistent with the proposed structures.

Mass spectra were obtained with a Fisons Instrument Trio 1000 spectrometer using thermospray ionisation.

Room temperature means 20°–25° C.

EXAMPLE 1

4-Methyl-1-[N-(2-methyl-1,2,3,4-tetrahydroisoquinoline-7-sulphonyl)-3-(1-amidino-1,2,5,6-tetrahydro-3-pyridyl)-(S)-alanyl]-1,2,3,6-tetrahydropyridine-2(R)-carboxylic acid dihydrochloride 1M Aqueous sodium hydroxide solution (12.5 ml, 12.5 mmol) was added dropwise with stirring to an ice-cooled solution of the title compound of Preparation 25 (1.57 g, 2.5 mmol) in water (10 ml) and the reaction mixture allowed to warm to room temperature. After 1.5 hours, the solution was extracted with dichloromethane (2×15 ml) and then acidified to pH2 with 1M hydrochloric acid (13 ml). The solution was evaporated to dryness under reduced pressure and residual traces of water removed azeotropically with 2-propanol. The dry residue was extracted with dichloromethane:2-propanol (1:1), then the combined extracts filtered and the filtrate evaporated under reduced pressure to yield the title compound (1.38 g, 90%) as a white powder. Rf 0.36 (SS 27). Found: C,48.46; H,6.11; N,12.24. $C_{26}H_{36}N_6O_5S$; 2HCl; $H_2O$; 0.33 $C_3H_8O$; 0.25 $CH_2Cl_2$ requires C,48.35; H,6.43; N,12.41%.

EXAMPLE 2

4-Methyl-1-[N-(3-methyl-2,3,4,5-tetrahydro-1H-3-benzazepine-7-sulphonyl)-3-(1-amidino-1,2,5,6-tetrahydro-3-pyridyl)-(S)-alanyl]-1,2,3,6-tetrahydropyridine-2(R)-carboxylic acid dihydrochloride The title compound (0.6 g, 88%) was obtained from the title compound of Preparation 33 (0.7 g, 1 mmol),using the procedure of Example 1, as a white powder. Rf 0.27 (SS 27). Found: C,48.93; H,6.76; N, 11.84. $C_{27}H_{38}N_6O_5S$; 2HCl;

$H_2O$; 0.33 $C_3H_8O$; 0.25 $CH_2Cl_2$ requires C,49.10; H,6.58; N,12.16%. m/e 559.3 $(M+H)^+$.

EXAMPLE 3

4(R)-Methyl-1-[N-(2-methyl-1,2,3,4-tetrahydroisoquinoline-7-sulphonyl)-3-(1-amidino-1,2,5,6-tetrahydro-3-pyridyl)-(S)-alanyl]piperidine-2 (R)-carboxylic acid dihydrochloride The title compound (0.15 g, 100%) was obtained from the title compound of Preparation 43 (0.16 g, 0.2 mmol), using the procedure of Example 1, as a white powder. Rf 0.33 (SS 27). Found: C,48.06; H,6.67; N,12.00. $C_{26}H_{38}N_6O_5S$; 2HCl; $H_2O$; 0.30 $C_3H_8O$; 0.25 $CH_2Cl_2$ requires C,48.17; H,6.68; N,12.41 %. m/e 547.4 $(M+H)^+$.

EXAMPLE 4

4-Methyl-1-[N-(2-methyl-1,2,3,4-tetrahydroisoquinoline-7-sulphonyl)-3-(1-amidino-1,2,5,6-tetrahydro-3-pyridyl)-(S)-alanyl]-1,2,3,6-tetrahydropyridine-2(S)-carboxylic acid dihydrochloride The title compound (496 mg, 84%) was obtained from the title compound of Preparation 62 (576 mg, 0.91 mmol), using the procedure of Example 1, as a white powder. Rf 0.41 (SS27). Found: C,48.07; H,6.31; N,12.74. $C_{26}H_{36}N_6O_5S$; 2HCl; $H_2O$; 0.125 $CH_2Cl_2$ requires C,48.55; H,6.28; N, 13.00% m/e 545 $(M+H)^+$.

EXAMPLE 5

4(R)-Methyl-1-[N-(2-methyl-1,2,3,4-tetrahydroisoquinoline-7-sulphonyl)-3-(1-amidino-1,2,5,6-tetrahydro-3-pyridyl)-(S)-alanyl]piperidine-2 (S-carboxylic acid dihydrochloride The title compound (300 mg, 79%) was obtained from the title compound of Preparation 63 (360 mg, 0.57 mmol), using the procedure of Example 1, as a white powder. Rf 0.39 (SS27). Found: C,46.85; H,6.76; N,12.98. $C_{26}H_{38}N_6O_5S$; 2HCl; $2H_2O$; 0.15 $CH_2Cl_2$ requires C,46.99; H,6.68; N,1257%.

EXAMPLE 6

4(S)-Methyl-1-[N-(2-methyl-1,2,3,4-tetrahydroisoquinoline-7-sulphonyl)-3-(1-amidino-1,2,5,6-tetrahydro-3-pyridyl)-(S)-alanyl]piperidine-2 (R)-carboxylic acid dihydrochloride The title compound (270 mg, 92%) was obtained from the title compound of Preparation 64 (330 mg, 0.48 mmol), using the procedure of Example 1, as a white powder. Rf 0.37 (SS 27). Found: C,46.76; H,6.54; N,12.39. $C_{26}H_{38}N_6O_5S$; 2HCl; 1.50 $H_2O$; 0.35 $CH_2Cl_2$ requires C,46.79; H,6.51; N,12.43%.

PREPARATION 1

2-Trifluoroacetyl-1,2,3,4-tetrahydroisoquinoline-7-sulphonyl chloride (a) 2-Trifluoroacetyl-1,2,3,4-tetrahydroisoquinoline This intermediate was obtained by the method described in J. Med. Chem., 1980, 23, 837 and used directly in step (b).
(b) The title compound was also obtained by the method described in J. Med. Chem., 1980, 23, 837, using the intermediate from (a) above, as a white solid (52.9% yield based on 1,2,3,4-tetrahydroisoquinoline), m.p. 104°–105° C., after crystallisation from ether. Rf 0.25 (SS 1).

PREPARATION 2

2-Trifluoroacetyl-1,2,3,4-tetrahydroisoquinoline-6-sulphonyl chloride

Crystallisation of material recovered from the mother-liquors of Preparation 1(b), from diisopropyl ether, afforded the title compound (3.6% yield based on 1,2,3,4-tetrahydroisoquinoline), m.p. 110°–112° C. Rf 0.36 (SS 1).

PREPARATION 3

3-Trifluoroacetyl-2,3,4,5-tetrahydro-1H-3-benzazepine-7-sulphonyl chloride (a) 2,3,4,5-Tetrahydro-1H-3-benzazepine This starting material was obtained by the method described in Helv. Chim. Acta, 1935, 18, 1388.

(b) 3-Trifluoroacetyl-2,3,4,5-tetrahydro-1H-3-benzazepine

Trifluoroacetic anhydride (6.0 g, 28.56 mmol) was added dropwise over 20 minutes to a stirred, ice-cooled solution of the material from (a) above (4.2 g, 28.56 mmol) and N-methylmorpholine (2.89 g, 28.56 mmol) in dichloromethane (45 ml). After 2.5 hours at room temperature, the reaction solution was washed successively with water, 1M aqueous citric acid solution and water, dried ($MgSO_4$) and evaporated under reduced pressure to yield a yellow solid, which was triturated with hot hexane. Filtration, concentration and cooling of the combined hexane solutions afforded the required product (5.96 g) as a pale yellow solid, m.p. 78°–80° C. Found: C,58.85; H,4.93; N,5.75. $C_{12}H_{12}F_3NO$ requires C,59.25; H,4.97; N,5.76%.

(c) Chlorosulphonic acid (10.4 ml, 0.156 mol) was added dropwise to a stirred, cold solution of the product from (b) above (5.85 g, 11.7 mmol) in dichloromethane, whilst ensuring that the temperature of the reaction mixture was held between −12° and −8° C. After 2 days at room temperature, the reaction solution was poured onto ice and the aqueous phase separated and extracted with dichloromethane. The combined organic extracts were dried ($MgSO_4$) and evaporated under reduced pressure to provide an oil (7.9 g) which was purified by chromatography on silica gel, using a mixture of hexane and ether (1:3) as eluant, to give the title compound as a colourless oil which eventually solidified. Crystallisation of a sample from diisopropyl ether produced a white solid, m.p. 87°–88° C. Found: C,41.75; H,3.18; N,3.92. $C_{12}H_{11}ClF_3NO_3S$ requires C,42.17; H,3.24; N,4.10%.

PREPARATION 4

1(R,S)-Methoxymethyl-2-trifluoroacetyl-1,2,3,4-tetrahydroisoquinoline-7-sulphonyl chloride (a) N-Methoxyacetyl-2-phenylethylamine Methoxyacetyl chloride (19.57 g, 0.18 mol) was added over 10 minutes to a stirred, ice-cooled solution of 2-phenylethylamine (21.85 g, 0.18 mol) and N-ethyldiisopropylamine (23.26 g, 0.18 mol) in dichloromethane (200 ml). After 2 hours at room temperature, the solvent was removed under reduced pressure and the residue partitioned between ether and water. The organic phase was washed successively with 1M aqueous citric acid solution, water, saturated aqueous sodium bicarbonate solution and water, dried (MgSO$_4$) and evaporated under reduced pressure to provide the required product (29.65 g) as an oil. Rf 0.32 (SS 2), which was used without further purification in the next step.

(b) 1-Methoxymethyl-3,4-dihydroisoquinoline

Phosphorous pentoxide (25 g, 0.176 mol) was added to a stirred solution of the product from (a) above (14.47 g, 0.075 mol) in xylene (35 ml) and the resulting mixture heated under reflux for 2.5 hours. The solvent was decanted from the resulting black gum which was triturated with xylene and then, when cool, with ether. Water was then carefully added, with ice-cooling, and the resulting mixture basified with 2M aqueous sodium hydroxide solution and then extracted with ether. The extract was washed with water, dried (MgSO$_4$) and evaporated under reduced pressure to give a brown oil (13.4 g) which was purified by chromatography on silica gel, using ether as eluant, to afford the required compound (5.88 g) as an orange oil. Rf 0.28 (SS 2).

(c) 1(R,S)-Methoxymethyl-1,2,3,4-tetrahydroisoquinoline

Sodium triacetoxyborohydride (8.11 g, 38.3 mmol) was added to a stirred, ice-cooled solution of the product from (b) above (6.1 g, 34.8 mmol) in methanol (80 ml), then the resulting mixture stirred for 18 hours at room temperature before being quenched with water. The bulk of the solvent was removed under reduced pressure, then the residue basified with 1M aqueous sodium hydroxide solution and extracted with dichloromethane. The extract was washed with saturated brine, dried (MgSO$_4$) and evaporated under reduced pressure to furnish the required product (6.19 g) as an orange oil. Rf 0.25 (SS 3), m/e 178 (M+H)$^+$, which was used without further purification in the next step.

(d) 1(R,S)-Methoxymethyl-2-trifluoroacetyl-1,2,3,4-tetrahydroisoquinoline

Trifluoroacetic anhydride (10.26 ml, 72.6 mmol) was added dropwise over 0.5 hour to a stirred, ice-cooled solution of the product from (c) above (12.26 g, 69.17 mmol) and N-methylmorpholine (7.35 g, 72.6 mmol) in dichloromethane (150 ml). After 2 hours at room temperature, the solvent was removed under reduced pressure and the residue partitioned between ether and water. The organic phase was washed successively with water basified to pH ca. 8 with sodium bicarbonate, 1M aqueous citric acid solution and water, dried (MgSO$_4$) and evaporated under reduced pressure to provide an oil (19.45 g) which was purified by chromatography on silica gel, using a mixture of hexane and ether (4:1) as eluant, to give the required compound (16.16 g) as a clear oil. Rf 0.27 (SS 4). Found: C,56.83; H,5.19; N,5.02. C$_{13}$H$_{14}$F$_3$NO$_2$ requires C,57.14; H,5.16; N,5.12%.

(e) The title compound was obtained from the product of (d) above, using the method of Preparation 3(c), as a pale yellow oil which solidified when chilled. Rf 0.35 (SS 5).

PREPARATION 5

1(R,S)-(N,N-Dimethylcarbamoylmethyl)-2-trifluoroacetyl-1,2,3,4-tetrahydroisoquinoline-7-sulphonyl chloride (a) 1(R,S)-(N,N-Dimethylcarbamoylmethyl)-2-trifluoroacetyl-1,2,3,4-tetrahydroisoquinoline 1-Ethoxycarbonylmethyl-1,2,3,4-tetrahydroisoquinoline (13.15 g, 60 mmol), obtained by the method described in J. Org. Chem., 1965, 30, 3667, was dissolved in a 30% solution of dimethylamine in ethanol (100 ml). Dimethylamine (32 g) was added and the reaction mixture heated in a steel bomb at 120° C. for 24 hours and at 150° C. for a further 24 hours, then evaporated under reduced pressure to provide the required crude amide (12.9 g) as an oil, Rf 0.13 (SS 3) plus trace of ester starting material at Rf 0.33, which was used without further purification in the next step.

Trifluoroacetic anhydride (12.12 g, 72 mmol) was added dropwise over 0.5 hour to a stirred, ice-cooled solution of the crude amide (12.9 g) and N-ethyidiisopropylamine (10.34 g, 80 mmol) in dichloromethane (120 ml). After 3 hours at room temperature, the solvent was removed under reduced pressure and the residue partitioned between ether and water. The organic phase was washed successively with water, 5% aqueous sodium bicarbonate solution, 1M aqueous citric acid solution and water, dried (MgSO$_4$) and evaporated under reduced pressure to give an orange oil which was purified by chromatography on silica gel, using a mixture of hexane and ethyl acetate (3:7) as eluant, to furnish the required compound (14.3 g). Rf 0.35 (SS 7). Found: C,56.88; H,5.38; N,8.85. C$_{15}$H$_{17}$F$_3$N$_2$O$_2$ requires C,57.32; H,5.45; N,8.91%.

(b) The title compound (84% yield) was obtained from the product of (a) above, using the procedure of Preparation 3(c), as a white foam. Rf 0.47 (SS 7).

PREPARATION 6

5-Methyl-2-trifluoroacetyl-1,2,3,4-tetrahydroisoquinoline-8-sulphonyl chloride (a) 5-Methylisoquinoline A 3M solution of methyl magnesium iodide in ether (50 ml, 0.15 mol) was added dropwise to a stirred, ice-cooled solution of 5-bromoisoquinoline (21 g, 0.10 mol), obtained by the method described in J. Org. Chem., 1964, 29, 329, and [1,3-bis(diphenylphosphino)propane]nickel(II) chloride (400 mg, 0.7 mmol) in anhydrous ether and the reaction mixture heated under reflux for 5 days, allowed to cool, then poured into water (500 ml). The organic phase was separated, combined with ether extracts of the aqueous phase, washed with saturated brine, dried (MgSO$_4$) and evaporated under reduced pressure to yield an oil, chromatography of which on silica gel, using a 5–50% ether in hexane elution gradient, provided the required product (8.4 g). Rf 0.40 (SS 8), m/e 144 (M+H)$^+$. Found: C,79.57; H,6.26; N,8.61. C$_{10}$H$_9$N; 0.27 C$_4$H$_8$O$_2$ requires C,79.70; H,6.74; N,8.39%.

However, the major component of the chromatographic purification procedure was a mixture (18.4 g) of product and starting material which, on crystallisation from hexane, afforded a 2:1 mixture (14.8 g) of 5-bromoisoquinoline and 5-methylisoquinoline.

(b) A stirred, ice-cooled solution of the above 2:1 mixture (14.3 g) in dichloromethane (150 ml) was saturated with hydrogen chloride and then evaporated under reduced pressure to afford the corresponding hydrochloride salt which was collected and dried. A stirred mixture of platinum oxide (1 g) and a solution of the preceding hydrochloride salt in ethanol (150 ml) was hydrogenated for 30 hours at 50 psi (3.45 bar) and room temperature, then filtered. The filtrate was evaporated under reduced pressure and the residue chromatographed on silica gel, using a mixture of dichloromethane:methanol: 0.880 aqueous ammonia solution (90:10:1) as eluant, to give an 85:15 mixture (5.62 g) of 5-methyl-1,2,3,4-tetrahydroisoquinoline and 5-bromo-1,2,3,4-tetrahydroisoquinoline as an oil; major component: Rf 0.32 (SS 9), m/e 148 (M+H)$^+$.

The above 85:15 mixture was converted to the corresponding 2-trifluoroacetyl derivative mixture, using the procedure described in Preparation 3(b), to afford an oil; major component: Rf 0.90 (SS 10), m/e 244 (M+H)$^+$.

The above crude mixture containing 85% of 5-methyl-2-trifluoroacetyl-1,2,3,4-tetrahydroisoquinoline, was chlorosulphonated following the procedure described in Preparation 3(c) to provide a yellow solid which, on purification by chromatography on silica gel using an elution gradient of 10–50% ethyl acetate in hexane, gave the title compound as a white solid, m.p. 152°–153° C. Found: C,42.18; H,3.24; N,4.10. $C_{12}H_{11}Cl\ F_3NO_3S$ requires C,42.12; H,3.10; N,3.85%.

PREPARATION 7

N-t-Butoxycarbonyl-3-(3-pyridyl)-(S)-alanine

Anhydrous potassium carbonate (7.5 g, 54 mmol) was added to a stirred, ice-cooled suspension of 3-(3-pyridyl)-(S)-alanine (Int. J. Pept. Prot. Res.; 1987, 29, 118; 9 g, 54 mmol) in water (50 ml), followed by the dropwise addition of a solution of di-t-butyl dicarbonate (18 g, 82 mmol) in 1,4-dioxan (25 ml) over 10 minutes. The resulting mixture was allowed to warm to room temperature and stir for 18 hours. The reaction mixture was concentrated by evaporation of the bulk of the 1,4-dioxan under reduced pressure and extracted with ethyl acetate (2×20 ml). The pH of the aqueous solution was adjusted to ca. 3 with solid citric acid, solid sodium chloride added to saturation and extraction with ethyl acetate (5×20 ml) effected. The combined organic extracts were dried ($MgSO_4$), filtered and evaporated to low bulk under reduced pressure, whereupon the product started to crystallise. After chilling at 0° C. for 1 hour, the crystals were collected, washed with ether and dried to give the required product (10.36 g, 72%). Rf 0.34 (SS 13).

$[\alpha]_D^{25}$+10° (c=0.1, $CH_3OH$). Found: C,58.69; H,7.17; N,10.50. $C_{13}H_{18}N_2O_4$ requires C,58.63; H,6.81; N,10.52%.

PREPARATION 8

N-t-Butoxycarbonyl-3-(3-pyridyl)-(S)-alanine t-butyl ester

To a stirred, ice-cooled solution of the title compound of Preparation 7 (10 g, 37.5 mmol) and t-butanol (14 g, 189 mmol) in dichloromethane (100 ml) was added 1-(3-dimethylaminopropyl)-3-ethylcarbodiimide hydrochloride (10 g, 52 mmol) and 4-dimethylaminopyridine (2.3 g, 18.8 mmol). The reaction mixture was allowed to warm to room temperature and stir for 18 hours. The solvent was evaporated under reduced pressure and the residue dissolved in ethyl acetate (100 ml). This solution was washed with water (2×30 ml) and brine (20 ml), dried ($MgSO_4$), filtered and evaporated under reduced pressure to yield an oil, which was purified by chromatography on silica gel using ethyl acetate:hexane (1:1) as eluant to afford the title compound (12.2 g, 100%) as a clear oil. Rf 0.59 (SS 26). m/e 322.9 $(M+H)^+$.

PREPARATION 9

N-t-Butoxycarbonyl-3-(1-benzyl-3-pyridinium)-(S)-alanine t-butyl ester bromide To a stirred solution of the title compound of Preparation 8 (1 g, 3.1 mmol) in dry ethanol (10 ml) at room temperature was added a solution of benzyl bromide (0.79 g, 4.6 mmol) in dry ethanol (2 ml), dropwise, over 5 minutes. After 18 hours the ethanol was evaporated under reduced pressure. The residue was dissolved in acetonitrile (10 ml) and the solution was extracted with hexane (3×5 ml) and then evaporated to dryness under reduced pressure. Solvent traces were removed azeotropically with dichloromethane to furnish the required product (1.23 g, 96%) as a white foam. Rf 0.49 (SS 13). Found: C,56.40; H,7.07; N,5.10. $C_{23}H_{33}BrN_2O_4$; 0.17 $CH_2Cl_2$ requires C,56.14; H,6.77; N,5.65%.

PREPARATION 10

N-t-Butoxycarbonyl-3-(1-benzyl-1,2,5,6-tetrahydro-3-pyridyl)-(S)-alanine t-butyl ester Sodium borohydride (0.19 g, 5 mmol) was added in two equal portions over 5 minutes to a stirred, ice-cooled solution of the title compound of Preparation 9 (0.7 g, 1.7 mmol) in ethanol (10 ml). After 1.5 hours, the solution was evaporated to dryness under reduced pressure. The residue was dissolved in dichloromethane (20 ml) and the solution was washed with saturated aqueous sodium bicarbonate solution and brine, dried ($MgSO_4$), filtered and evaporated under reduced pressure. The residue was purified by chromatography on silica gel, using an elution gradient of ethyl acetate:hexane (0:100 to 20:80), to afford the title compound (0.36 g, 91%) as an oil. Rf 0.42 (SS 8). m/e 417.3 $(M+H)^+$.

PREPARATION 11

3-(1-Benzyl-1 2,5,6-tetrahydro-3-pyridyl)-(S)-alanine t-butyl ester

The title compound of Preparation 10 (1 g, 2.4 mmol) was dissolved in 96% formic acid (10 ml) and the solution was stirred at room temperature for 4 hours. The formic acid was then removed under reduced pressure at ≦30° C. The residue was dissolved in 1M aqueous citric acid solution (20 ml) and the solution extracted with ethyl acetate (2×10 ml). The aqueous phase was basified to pH8 with solid sodium bicarbonate and extracted with dichloromethane (3×10 ml). The combined organic extracts were dried ($MgSO_4$), filtered and evaporated under reduced pressure to yield the required product (0.74 g, 97%) as an oil, which was used without further purification. Rf 0.73 (SS 9).

PREPARATION 12

N-(2-Trifluoroacetyl-1,2,3,4-tetrahydroisoquinoline-7-sulphonyl)-3-(1-benzyl-1,2,5,6-tetrahydro-3-pyridyl)-(S)-alanine t-butyl ester 2-Trifluoroacetyl-1,2,3,4-tetrahydroisoquinoline-7-sulphonyl chloride (Preparation 1; 2.26 g, 6.9 mmol) was added dropwise over 5 minutes as a solution in dichloromethane (5 ml) to a stirred, ice-cooled solution of the title compound of Preparation 11 (1.82 g, 5.7 mmol) and N-ethyldiisopropylamine (1.1 g, 8.5 mmol) in dichloromethane (10 ml). The resulting solution was allowed to warm to room temperature and stir for 18 hours. The solvent was evaporated under reduced pressure and the residue dissolved in ethyl acetate (30 ml). This solution was washed with water (10 ml), saturated aqueous sodium bicarbonate solution (2×10 ml) and saturated brine (10 ml), dried ($MgSO_4$), filtered and evaporated under reduced pressure. The residue was purified by chromatography on silica gel, using an elution gradient of ethyl acetate:hexane (10:90 to 50:50), to furnish the required product (3 g, 86%) as a white foam. Rf 0.63 (SS 26). Found: C,58.70; H,5.75; N,6.64. $C_{30}H_{36}F_3N_3O_5S$; 0.10 $CH_2Cl_2$ requires C,58.66; H,5.92; N,6.82%. m/e 608.4 $(M+H)^+$.

PREPARATION 13

N-(2-Trifluoroacetyl-1,2,3,4-tetrahydroisoquinoline-7-sulphonyl)-3-(1-benzyl-1,2,5,6-tetrahydro-3-pyridyl-(S)-alanine hydrochloride A stirred, ice-cooled solution of the title compound of Preparation 12 (3 g, 4.9 mmol) in dichloromethane (30 ml)

was saturated with hydrogen chloride and then allowed to attain room temperature. After 6 hours the solvent and excess hydrogen chloride were removed under reduced pressure. Residual traces of hydrogen chloride were removed azeotropically with dichloromethane to yield the title compound (3 g, 100%) as a white foam. Rf 0.29 (SS 13). Found: C,50.40; H,4.90; N,6.73. $C_{26}H_{28}F_3N_3O_5S$; HCl; 0.50 $CH_2Cl_2$ requires C,50.47; H,4.79; N,6.66%. m/e 552.4 $(M+H)^+$.

PREPARATION 14

4(R)-Methylpiperidine-2(R)-carboxylic acid ethyl ester

The title compound was obtained by the method described in Biochem. Biophys. Res. Comm., 1981, 101, 440.

PREPARATION 15

4-Methyl-1,2,3,6-tetrahydropyridine-2(R)-carboxylic acid ethyl ester hydrochloride (a) 4-Methyl-1-[1-(S)-phenylethyl]-1,2,3,6-tetrahydropyridine-2(R)-carboxylic acid ethyl ester
This intermediate was obtained by the method described in Tetrahedron:Asymmetry, 1991 2, 1263.

(b) A stirred solution of the above intermediate (13.56 g, 49.7 mmol) in toluene (150 ml), under nitrogen, was heated under reflux for 2 hours, using a Dean-Stark trap. 1,8-Bis(dimethylamino)naphthalene (1.08 g, 5.0 mmol) was then added, heating continued for a further 1 hour, the reaction mixture allowed to cool and the Dean-Stark trap removed. After the addition of 1-chloroethyl chloroformate (10.7 ml, 14.2 g, 99.5 mmol), the reaction mixture was stirred under reflux for 16 hours, allowed to cool, treated with absolute ethanol (80 ml), stirred under reflux for 2 hours more and evaporated under reduced pressure. The residue was partitioned between ethyl acetate (100 ml) and 1M hydrochloric acid (50 ml), then the aqueous phase separated, neutralised with solid sodium bicarbonate and extracted with dichloromethane (3×200 ml). Evaporation under reduced pressure of the dried ($MgSO_4$), combined extracts provided a brown residue which was purified by chromatography on silica gel, using a 0–5% methanol in dichloromethane elution gradient, and then converted to the required hydrochloride salt using excess ethereal hydrogen chloride. The product was further purified by dissolution in dichloromethane (20 ml), filtration (to remove residual silica gel), dilution of the filtrate with ether (200 ml), filtration, washing of the precipitate with ether and drying in vacuo. A sample of this purified product (5.77 g) was crystallised from a mixture of ether and ethanol to afford the title compound as white crystals, m.p. 110°–111° C. Rf 0.35 (SS 3).
$[\alpha]_D^{25}$ +113.7° (c=1.0, $CH_3CH_2OH$). Found: C,52.79; H,7.94; N,6.68. $C_9H_{15}NO_2$; HCl requires C,52.55; H,7.84; N,6.81%.

PREPARATION 16

4-Methyl-1,2,3,6-tetrahydropyridine-2(R)-carboxylic acid methyl ester p-toluenesulphonate (a) 4-Methyl-1-[1-(S)-phenylethyl]-1,2,3,6-tetrahydropyridine-2(R)-carboxylic acid methyl ester
This intermediate was obtained by the method described in Tetrahedron, 1992, 48, 9707 as the major diastereoisomer of a mixture also containing the 1(S), 2(S)-diastereoisomer (ratio 3.7:1 by NMR spectroscopy).

Formation of the hydrochloride salt using hydrogen chloride in toluene, followed by two crystallisations from ethyl acetate and liberation of the free base, afforded the required 1(S),2(R)-diastereoisomer in sufficiently stereochemically pure form (S,R:S,S>97:3) for further processing.

(b) N-Deprotection of the previous product was effected by the methodology described in J. Org. Chem., 1984, 49, 2081, (see also Preparation 21), using 1-chloroethyl chloroformate as the "debenzylation" reagent, followed by conversion of the resulting hydrochloride salt to the corresponding p-toluenesulphonate, m.p. 141°–143° C. Rf 0.61 (SS 9).

PREPARATION 17

4-Methyl-1,2,3,6-tetrahydropyridine-2(R,S)-carboxylic acid ethyl ester hydrochloride (a) 1-Benzyl-4-methyl-1,2,3,6-tetrahydropyridine-2(R,S)-carboxylic acid ethyl ester
This intermediate was obtained by the method described in Tetrahedron Asymmetry, 1991, 2, 1263.

(b) The title compound (82% yield) was obtained from the intermediate of (a) above, using the method of Preparation 15(b), as a white solid, m.p. 130°–130.5° C. Rf 0.35 (SS 3).

PREPARATION 18

4-Methyl-1,2,3,6-tetrahydropyridine-2(S)-carboxylic acid ethyl ester hydrochloride (a) 1-Benzyl-4-methyl-1,2,3,6-tetrahydropyridine-2(R,S)-carboxylic acid hydrochloride A stirred solution of 1-benzyl-4-methyl-1,2,3,6-tetrahydropyridine-2(R,S)-carboxylic acid ethyl ester (Preparation17(a); 20.1 g, 77.5 mmol) in 5M hydrochloric acid (200 ml) was heated at 100° C. for 4.5 hours and then evaporated to dryness under reduced pressure. Residual water was removed azeotropically using dichloromethane followed by toluene to give the required product (24.0 g) as a white foam, Rf 0.40 (SS 13), which was used without further purification in the next step.

(b) 1-Benzyl-4-methyl-1,2,3,6-tetrahydropyridine-2(R,S)-carboxylic acid N-acetyl-(1R,2S)-ephedrine ester 1,3-Dicyclohexylcarbodiimide (20.6 g, 0.1 mol) was added to a stirred solution of the product from (a) above (24.0 g, 89.6 mmol), N-acetyl-(1R,2S)-ephedrine (18.47 g, 89.2 mmol), obtained by the method described in J. Amer. Pharmaceut. Assoc., 1952, 41, 545, (see J. Med. Chem., 1965, 8, 466), N-ethyldiisopropylamine (12.9 g, 0.1 mmol) and 4-dimethylaminopyridine (9.51 g, 77.5 mmol) in dichloromethane (250 ml). After 3 days at room temperature, the reaction mixture was filtered and the filtrate evaporated to dryness under reduced pressure. The residue was partitioned between ethyl acetate and water, then the organic phase separated, washed with water, dried ($MgSO_4$) and evaporated under reduced pressure to give the crude product, which was purified by chromatography on silica gel, using ether as eluant, to furnish the required pure product (25.5 g) as an oil. Rf 0.35 (SS 2). Found: C,73.34; H,7.71; N,5.73. $C_{26}H_{32}N_2O_3$; 0.30 $C_4H_{10}O$ requires C,73.78; H,7.91; N,6.3%.

(c) 4-Methyl-1-(2,2,2-trichloroethoxycarbonyl)-1,2,3,6-tetrahydropyridine-2(R,S)-carboxylic acid N-acetyl-(1R,2S)-ephedrine ester Sodium bicarbonate (11.21 g, 133 mmol), then 2,2,2-trichloroethyl chloroformate (11.7 ml, 17.97 g, 84.8 mmol), were added to a stirred solution of the product from (b) above (25.48 g, 60.6 mmol) in dry dichloromethane (200 ml) and the resulting mixture was heated under reflux for 22 hours. The solvent was removed under reduced pressure and the residue partitioned between ethyl acetate and water. The separated organic phase was washed with saturated brine, dried (MgSO$_4$) and evaporated under reduced pressure, then the residue purified by chromatography on silica rel, using ether as eluant, to afford the required product (28.1 g) as a gum. Rf 0.40 (SS 2). Found: C,52.10; H,5.38; N,5.24. C$_{22}$H$_{27}$Cl$_3$N$_2$O$_5$ requires C,52.24; H,5.38; N,5.54%.

(d) 4-Methyl-1,2,3,6-tetrahydropyridine-2(R)-carboxylic acid N-acetyl-(1R,2S)-ephedrine ester and 4-methyl-1,2,3,6-tetrahydropyridine-2(S)-carboxylic acid N-acetyl-(1R,2S)-ephedrine ester 1M Aqueous potassium dihydrogen phosphate solution (40 ml, 40 mmol), then zinc dust (40 g, 610 mmol), were added to a rapidly stirred solution of the product from (c) above (32.9 g, 65 mmol) in tetrahydrofuran (200 ml). After 1 hour at room temperature, the reaction mixture was filtered and the bulk of the organic solvent removed under reduced pressure, then the residue basified with saturated aqueous sodium bicarbonate solution and extracted with ethyl acetate. The extract was washed with saturated brine, dried (MgSO$_4$) and evaporated under reduced pressure to give an oil (21.46 g), which was chromatographed on silica gel using an elution gradient of ethanol:ethyl acetate (1:4 to 3:7), to provide firstly the 2(R)-diastereoisomeric ester (2.75 g), Rf 0.30 (SS 14), m/e 331 (M+H)$^+$, followed by the 2(S)-diastereoisomeric ester (2.90 g), Rf 0.22 (SS 14), m/e 331 (M+H)$^+$, each as a pale yellow oil.

(e) N-t-Butoxycarbonyl-4-methyl-1,2,3,6-tetrahydropyridine-2(S)-carboxylic acid N-acetyl-(1R,2S)-ephedrine ester Di-t-butyl dicarbonate (4.4 g, 20.2 mmol) was added to a stirred solution of the 2(S)-ester product from (d) above (5.13 g, 15.5 mmol) and N-methylmorpholine (2.04 g, 20.2 mmol) in dichloromethane (40 ml). After 5 hours at room temperature, more di-t-butyl dicarbonate (1.35 g, 6.2 mmol) was added and the reaction mixture stirred for a further 15 hours before removal of the solvent under reduced pressure. The residual mixture was partitioned between ethyl acetate and water, then the organic phase washed successively with 1M aqueous citric acid solution, saturated aqueous sodium bicarbonate solution and saturated brine, dried (MgSO$_4$) and evaporated under reduced pressure to give a gum which was purified by chromatography on silica gel, using ether as eluant, to afford the required product (6.02 g) as a gum. Rf 0.45 (SS 2). Found: C,66.84; H,7.97; N,6.50. C$_{24}$H$_{34}$N$_2$O$_5$ requires C,66.95; H,7.96; N,6.51%.

(f) N-t-Butoxycarbonyl-4-methyl-1,2,3,6-tetrahydropyridine-2 (S)-carboxylic acid 1M Aqueous sodium hydroxide solution (69 ml, 69 mmol) was added to a stirred solution of the product from (e) above (5.97 g, 13.9 mmol) in 1,4-dioxan (60 ml). After 3 hours at room temperature, solid citric acid (5.53 g, 26 mmol) was added and the bulk of the solvent removed under reduced pressure. The residual suspension was basified to pH 10 with 1M aqueous sodium hydroxide solution, washed with dichloromethane, acidified to pH 3 with solid citric acid and extracted with ethyl acetate. The organic extract was washed with saturated brine, dried (MgSO$_4$) and evaporated under reduced pressure to provide the required product (3.47 g) as a gum. Rf 0.60 (SS 17).

(g) N-t-Butoxycarbonyl-4-methyl-1,2,3,6-tetrahydropyridine-2(S)-carboxylic acid ethyl ester 1,3-Dicyclohexylcarbodiimide (4.3 g, 20.8 mmol) was added to a stirred solution of the product from (f) above (3.35 g, 13.9 mmol), ethanol (4.1 ml, 69.4 mmol) and 4-dimethylaminopyridine (1.7 g, 13.9 mmol) in dichloromethane (40 ml). After 18 hours at room temperature, glacial acetic acid (0.4 ml) was added and the reaction mixture stirred for a further 0.5 hour before being filtered. The residue obtained by evaporation of the filtrate under reduced pressure was partitioned between ether and water, then the organic phase washed successively with 1M aqueous citric acid solution, saturated aqueous sodium bicarbonate solution and saturated brine, dried (MgSO$_4$) and evaporated under reduced pressure to give an oil (5.15 g), which was purified by chromatography on silica gel, using hexane:ether (4:1) as eluant, to furnish the required product (3.4 g) as a clear oil. Rf 0.30 (SS 4). m/e 270 (M+H)$^+$.

(h) A stirred, ice-cooled solution of the product from (g) above (3.13 g, 11.62 mmol) in ethyl acetate (30 ml) was satured with hydrogen chloride over 0.5 hour and then stood at room temperature for a further 2 hours. The solvent was evaporated under reduced pressure and the residue crystallised from a mixture of ether and ethanol to afford the title compound (2.20 g) as white crystals, m.p. 108°–109° C. Rf 0.35 (SS 3).

$[\alpha]_D^{25}$ –106.5° C. (c=1.0, CH$_3$CH$_2$OH). Found: C,52.49; H,7.90; N,6.70. C$_9$H$_{15}$NO$_2$; HCl requires C,52.55; H,7.84; N,6.81%.

The compound obtained by carrying out steps (e), (f), (g) and (h) on the 2(R)-ester from (d) above was found to be identical with the title compound of Preparation 15.

PREPARATION 19

4-Ethyl-1,2,3,6-tetrahydropyridine-2(R,S)-carboxylic acid ethyl ester hydrochloride (a) 2-Cyano-4-ethyl-1-methyl-1,2,3,6-tetrahydropyridine hydrochloride Methyl iodide (74.7 ml, 170.33 g, 1.22 mol) was cautiously added portionwise to a stirred solution of 4-ethylpyridine (107.2 g, 1 mol) in acetone (500 ml), the resulting mixture heated under reflux for 2 hours and allowed to cool, then a portion of solvent (ca. 100 ml) removed under reduced pressure. Addition of ether (1.0 l), collection and washing with ether of the precipitate, followed by drying in vacuo, provided the required quaternary iodide (245 g) as a very hygroscopic solid. 6M Hydrochloric acid (130 ml) was slowly added to a stirred solution of potassium cyanide (130 g, 2.5 mol) in water (260 ml) covered by a layer of ether (400 ml), ensuring that the temperature was maintained below 15° C. Successive, portionwise addition of the above quaternary salt (139.49 g, 0.56 mol) and sodium borohydride (27 g, 0.71 mol) over 15 minutes gave a milky mixture, which was stirred at ca. 10° C. for 0.5 hour and then at room temperature for a further 4 hours. The ether phase was removed by suction and combined with an ether extract of the aqueous phase, then washing with saturated brine and drying (MgSO$_4$) effected. The ether solution was ice-cooled, with stirring, and methyl iodide (6 ml) added to precipitate any unwanted 4-ethyl-1-methylpiperidine as the derived quaternary iodide. Filtration, followed by treatment of the filtrate with excess 1M ethereal hydrogen chloride, afforded the required product (43.77 g) as an oil, Rf 0.20 (SS 18), which was used without further purification in the next step.

(b) 4-Ethyl-1-(2,2,2-trichloroethoxycarbonyl)-1,2,3,6-tetrahydropyridine-2(R,S)-carboxylic acid ethyl ester A stirred solution of the product from (a) above (43.5 g, 0.23 mol) in ethanol (100 ml) was saturated with hydrogen chloride, heated under reflux for 6.5 hours and then evaporated to dryness under reduced pressure. The residue was basified with aqueous sodium carbonate solution, then extraction with ethyl acetate effected. The extract was washed with saturated brine, dried (MgSO$_4$) and evaporated under reduced pressure to give the crude ethyl ester, which was partially purified by chromatography on silica gel, using hexane:ethyl acetate:diethylamine (90:5:2) as eluant, to provide an oil (8.0 g).

Sodium carbonate (10.0 g, 94 mmol) and 2,2,2-trichloroethyl chloroformate (13.0 g, 61 mmol) were added successively to a stirred solution of the above crude ester (8.0 g, 40 mmol) in dichloromethane (200 ml) and the resulting mixture heated under reflux for 20 hours, then evaporated under reduced pressure. The residue was partitioned between ethyl acetate and water, then the organic phase dried (MgSO$_4$) and evaporated under reduced pressure to give an oil which was purified by chromatography on silica gel, using hexane:ethyl acetate (50:1) as eluant, to furnish the required product (4.8 g) as a colourless oil. Rf 0.25 (SS 19).

(c) 1M Aqueous potassium dihydrogen phosphate solution (70 ml, 70 mmol), then zinc dust (46 g, 700 mmol), were added to a rapidly stirred solution of the product from (b) above (4.76 g, 13.3 mmol) in tetrahydrofuran (220 ml). After 2 hours at room temperature more zinc dust (5 g, 76 mmol) was added and the reaction mixture stirred for a further hour before being filtered. The filter pad was washed with water and tetrahydrofuran, then the bulk of the organic solvent removed from the combined filtrate and washings. The residual mixture was acidified with 2M hydrochloric acid (30 ml), washed with ethyl acetate to remove starting material (2.32 g recovered), neutralised with solid potassium carbonate and extracted with dichloromethane. The combined organic extracts were washed with saturated brine, dried (MgSO$_4$), treated with excess ethereal hydrogen chloride and evaporated under reduced pressure. Purification of the residue by chromatography on silica gel, using dichloromethane:methanol (95:5) as eluant, furnished the title compound (330 mg), as a colourless waxy solid. m/e 184 (M+H)$^+$.

PREPARATION 20

4-Methyl-1-[N-(2-trifluoroacetyl-1,2,3,4-tetrahydroisoquinoline-7-sulphonyl)-3-(1-benzyl-1,2,5,6-tetrahydro-3-pyridyl)-(S)-alanyl]-1,2,3,6-tetrahydropyridine-2(R)-carboxylic acid methyl ester Dimethylformamide (0.25 ml) was added in one portion to a stirred, ice-cooled solution of the title compound of Preparation 13 (3 g, 5.1 mmol) and oxalyl chloride (2.6 g, 20.5 mmol) in dichloromethane (30 ml). After 2 hours at room temperature the solvent and excess oxalyl chloride were removed by evaporation under reduced pressure. Residual traces of oxalyl chloride were removed azeotropically with dichloromethane to give the crude acyl chloride as a foam, which was then dissolved in dichloromethane (30 ml). To this stirred, ice-cooled solution were added, successively, the title compound of Preparation 16 (1.83 g, 5.6 mmol) and N-ethyldiisopropylamine (2.3 g, 17.8 mmol). The resulting solution was stirred at room temperature for 18 hours and then evaporated under reduced pressure. The residue was dissolved in ethyl acetate (50 ml) and the solution washed successively with water, saturated aqueous sodium bicarbonate solution and saturated brine, dried (MgSO$_4$) and evaporated under reduced pressure to give the crude product, which was purified by chromatography on silica gel using an elution gradient of ethyl acetate:hexane (10:90 to 100:0) to afford the title compound (3 g, 85%) as a white foam. Rf 0.32 (SS 26). Found C,59.08; H,5.27; N,7.62. C$_{34}$H$_{39}$F$_3$N$_4$O$_6$S requires C,59.29; H,5.71; N,8.13%. m/e 689.1 (M+H)$^+$.

PREPARATION 21

4-Methyl-1-|N-(2-trifluoroacetyl-1,2,3,4-tetrahydroisoquinoline-7-sulphonyl)-3-(1,2,5,6-tetrahydro-3-pyridyl)-(S)-alanyl|-1,2,3,6-tetrahydropyridine-2(R)-carboxylic acid methyl ester 1-Chloroethyl chloroformate (0.93 g, 6.5 mmol) was added dropwise as a solution in dichloromethane (3 ml) to a stirred, ice-cooled solution of the title compound of Preparation 20 (3 g, 4.3 mmol) and 1,8-bis(dimethylamino)naphthalene (0.09 g, 0.4 mmol) in dichloromethane (12 ml). The resulting solution was allowed to warm to room temperature. After 3 hours the reaction mixture was washed with 1M aqueous citric acid solution (2×5 ml) and saturated brine (5 ml), dried (MgSO$_4$), filtered and evaporated under reduced pressure. The residue was dissolved in methanol (25 ml) and the solution heated to reflux for 45 minutes. The solvent was evaporated under reduced pressure and the crude product purified by chromatography on silica gel, using an elution gradient of dichloromethane:hexane (75:25 to 100:0), followed by dichloromethane:methanol:0.880 aqueous ammonia (99:1:0.5 to 95:5:0.5), to furnish the required product (2 g, 76%) as a white foam. Rf 0.24 (SS 9). Found: C,52.86; H,5.38; N,8.65. C$_{27}$H$_{33}$F$_3$N$_4$O$_6$S; 0.20 CH$_2$Cl$_2$ requires C,53.06; H,5.46; N,9.10%. m/e 599 (M+H)$^+$.

PREPARATION 22

4-Methyl-1-{N-[2-trifluoroacetyl-1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}-1,2,3,6-tetrahydropyridine-2(R)-carboxylic acid methyl ester A stirred, ice-cooled solution of the title compound of Preparation 21 (2 g, 3.3 mmol) in dichloromethane (20 ml) was treated sequentially with triethylamine (1 g, 9.9 mmol), bis t-butoxycarbonyl-S-methylisothiourea (J. Med. Chem., 1993, 36, 2956; 1.05 g, 3.6 mmol) and mercuric chloride (1 g, 3.7 mmol) and then allowed to warm to room temperature and stir for 18 hours. The reaction mixture was filtered and the filtrate washed successively with water (5 ml), 1M aqueous citric acid solution (5 ml) and saturated brine (5 ml), dried (MgSO$_4$), filtered and evaporated under reduced pressure. The residue was purified by chromatography on silica gel, using an elution gradient of ethyl acetate:hexane (0:100 to 80:20), to furnish the required product (2.4 g, 86%) as a white foam. Rf 0.33 (SS 12). Found: C,52.11; H,5.82; N,9.59. C$_{38}$H$_{51}$F$_3$N$_6$O$_{10}$S; 0.50 CH$_2$Cl$_2$ requires C,52.34; H,5.93; N,9.51%. m/e 841.1 (M+H)$^+$.

PREPARATION 23

4-Methyl-1-{N-[1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}-1,2,3,6-tetrahydropyridine-2(R)-carboxylic acid methyl ester A solution of sodium carbonate (1.2 g, 11.3 mmol) in water (15 ml) was added dropwise to a stirred solution of the title compound of Preparation 22 (2.4 g, 2.8 mmol) in methanol (25 ml) at room temperature. After 1.5 hours the bulk of the methanol was removed under reduced pressure. The remaining aqueous phase was extracted with ethyl acetate (2×10 ml) and the combined organic extracts were dried (MgSO$_4$), filtered and evaporated under reduced pressure. The residue was purified by chromatography on silica gel, using an elution gradient of dichloromethane:hexane (75:25 to 100:0), followed by dichloromethane:methanol:0.880 aqueous ammonia (95:5:0.5 to 90:10:1), to give the required product (2.07 g, 97%) as a white foam. Rf 0.40 (SS 9). Found: C,55.22; H,6.72; N,10.65. C$_{36}$H$_{52}$N$_6$O$_9$S; 0.50 CH$_2$Cl$_2$ requires C,55.67; H,6.78; N,10.67%.

PREPARATION 24

4-Methyl-1-{N-[2-methyl-1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}-1,2,3,6-tetrahydropyridine-2(R)-carboxylic acid methyl ester Aqueous formaldehyde solution (37% w/v, 0.9 ml, 11 mmol) was added to a stirred solution of the title compound of Preparation 23 (2.07 g, 2.7 mmol) in dichloromethane (20 ml) at room temperature then, after 20 minutes, sodium triacetoxyborohydride (0.82 g, 3.8 mmol) was added. After a further 2 hours, the reaction mixture was washed with saturated aqueous sodium bicarbonate solution (2×10 ml) and saturated brine (10 ml), dried (MgSO$_4$), filtered and evaporated under reduced pressure. The residue was purified by chromatography on silica gel, using an elution gradient of dichloromethane:hexane (75:25 to 100:0), followed by dichloromethane:methanol:0.880 aqueous ammonia (99:1:0.5 to 95:5:0.5), to afford the required product (1.95 g, 93%) as a white foam. Rf 0.54 (SS 9). Found: C,55.95; H,7.00; N,10.36. C$_{37}$H$_{54}$N$_6$O$_9$S; 0.50 CH$_2$Cl$_2$ requires C,56.19; H,6.92; N,10.48%.

PREPARATION 25

4-Methyl-1-[N-(2-methyl-1,2,3,4-tetrahydroisoquinoline-7-sulphonyl)-3-(1-amidino-1,2,5,6-tetrahydro-3-pyridyl)-(S)-alanyl]-1,2,3,6-tetrahydropyridine-2(R)-carboxylic acid methyl ester dihydrochloride A stirred, ice-cooled solution of the title compound of Preparation 24 (1.93 g, 2.5 mmol) in dichloromethane (30 ml) was saturated with hydrogen chloride. The solution was allowed to attain room temperature and after 5 hours the solvent and excess hydrogen chloride were removed under reduced pressure. Residual traces of hydrogen chloride were removed azeotropically with dichloromethane to furnish the product (1.57 g, 98%) as a white powder. Rf 0.22 (SS 24). Found: C,47.26; H,6.38; N,11.89. C$_{27}$H$_{38}$N$_6$O$_5$S;2HCl; H$_2$O; 0.50 CH$_2$Cl$_2$ requires C,47.72; H,6.26; N,12.14%.

PREPARATION 26

N-(3-Trifluoroacetyl-2,3,4,5-tetrahydro-1H-3-benzazepine-7-sulfonyl)-3-(1-benzyl-1,2,5,6-tetrahydro-3-pyridyl)-(S)-alanine t-butyl ester The title compound (1.9 g, 70%) was obtained from the title compounds of Preparation 3 (1.62 g, 4.7 mmol) and Preparation 11 (1.36 g, 4.3 mmol), using the procedure described in Preparation 12, as a white foam. Rf 0.65 (SS 26). Found C,59.14; H,6.09; N,6.54. C$_{31}$H$_{38}$F$_3$N$_3$O$_5$S;0.125 CH$_2$Cl$_2$ requires C,59.11; H,6.09; N,6.64%. m/e 622.1 (M+H)$^+$.

PREPARATION 27

N-(3-Trifluoroacetyl-2,3,4,5-tetrahydro-1H-3-benzazepine-7-sulfonyl)-3-(1-benzyl-1,2,5,6-tetrahydro-3-pyridyl)-(S)-alanine hydrochloride The title compound (1.85 g, 100%) was obtained from the title compound of Preparation 26 (1.89 g, 3 mmol), using the procedure described in Preparation 13, as a white foam. Rf 0.35 (SS 13). m/e 566.2 (M+H)$^+$.

PREPARATION 28

4-Methyl-1-[N-(3-trifluoroacetyl-2,3,4,5-tetrahydro-1H-3-benzazepine-7-sulphonyl)-3-(1-benzyl-1,2,5,6-tetrahydro-3-pyridyl)-(S)-alanyl]-1,2,3,6-tetrahydropyridine-2(R)-carboxylic acid methyl ester The title compound (1.7 g, 80%) was obtained from the title compounds of Preparation 27 (1.82 g, 3.0 mmol) and Preparation 16 (1.1 g, 3.3 mmol), using the procedure of Preparation 20, as a white foam. Rf 0.68 (SS 9). Found: C,58.50; H,5.43; N,7.39. C$_{35}$H$_{41}$F$_3$N$_4$O$_6$S; 0.10 CH$_2$Cl$_2$ requires C,59.10; H,5.83; N,7.87%. m/e 703.3 (M+H)$^+$.

PREPARATION 29

4-Methyl-1-[N-(3-trifluoroacetyl-2,3,4,5-tetrahydro-1H-3-benzazepine-7-sulphonyl)-3-(1,2,5,6-tetrahydro-3-pyridyl)-(S)-alanyl]-1,2,3,6-tetrahydropyridine-2(R)-carboxylic acid methyl ester The title compound (1.24 g, 78%) was obtained from the title compound of Preparation 28 (1.8 g, 2.5 mmol), using the procedure of Preparation 21, as a tan-coloured foam. Rf 0.21 (SS 9). Found: C,53.43; H,5.35; N,8.72. C$_{28}$H$_{35}$F$_3$N$_4$O$_6$S; 0.20 CH$_2$Cl$_2$ requires C,53.78; H,5.66; N,8.89%. m/e 613.3 (M+H)$^+$.

PREPARATION 30

4-Methyl-1-{N-[3-trifluoroacetyl-2,3,4,5-tetrahydro-1H-3-benzazepine-7-sulphonyl]-3-[1-(N,N'-di-t-butoxycarbonylamidino)-1,2,5,6-tetrahydro-3-pyridyl]-(S)-alanyl}-1,2,3,6-tetrahydropyridine-2(R)-carboxylic acid methyl ester The title compound (1.49 g, 87%) was obtained from the title compound of Preparation 29 (1.22 g, 2 mmol), using the procedure of Preparation 22, as a white foam. Rf 0.84 (SS 26). Found: C,52.72; H,5.81; N,9.36. C$_{39}$H$_{53}$F$_3$N$_6$O$_{10}$S; 0.50 CH$_2$Cl$_2$ requires C,52.86; H,6.06; N,9.36%.

PREPARATION 31

4-Methyl-1-{N -[2,3,4,5-tetrahydro-1H-3-benzazepine-7-sulphonyl]-3-[1-(N,N'-di-t-butoxycarbonylamidino)-1,2,5,6-tetrahydro-3-pyridyl]-(S)-alanyl}-1,2,3,6-tetrahydropyridine-2(R)-carboxylic acid methyl ester The title compound (0.94 g, 72%) was obtained from the title compound of Preparation 30 (1.47 g, 1.7 mmol), using the procedure of Preparation 23, as a white foam. Rf 0.38 (SS 9). Found: C,56.08; H,7.22; N,10.15. C$_{37}$H$_{54}$N$_6$O$_9$S; 0.50 CH$_2$Cl$_2$ requires C,56.19; H,6.91; N,10.48%.

PREPARATION 32

4-Methyl-1-{N-[3-methyl-2,3,4,5-tetrahydro-1H-3-benzazepine-7-sulphonyl]-3-[1-(N,N'-di-t-butoxycarbonylamidino)-1,2,5,6-tetrahydro-3-pyridyl]-(S)-alanyl}-1,2,3,6-tetrahydropyridine-2(R)-carboxylic acid methyl ester The title compound (0.92 g, 97%) was obtained from the title compound of Preparation 31 (0.93 g, 1.2 mmol), using the procedure of Preparation 24, as a white foam. Rf 0.49 (SS 9). Found: C,56.45; H,7.18; N,9.89. $C_{38}H_{56}N_6O_9S$; $H_2O$; 0.33 $CH_2Cl_2$ requires C,56.19; H,7.21; N,10.25%. m/e 773.4 $(M+H)^+$.

PREPARATION 33

4-Methyl-1-[N-(3-methyl-2,3,4,5-tetrahydro-1H-3-benzazepine-7-sulphonyl)-3-(1-amidino-1,2,5,6-tetrahydro-3-pyridyl)-(S)-alanyl]-1,2,3,6-tetrahydropyridine-2(R)-carboxylic acid methyl ester dihydrochloride The title compound (0.71 g, 83%) was obtained from the title compound of Preparation 32 (0.92 g, 1.2 mmol), using the procedure of Preparation 25, as a white powder. Rf 0.39 (SS 28). Found: C,48.11; H,6.88; N,11.44. $C_{28}H_{40}N_6O_5S$; 2HCl; 0.50 $CH_2Cl_2$ requires C,47.87; H,6.48; N,11.75%. m/e 573.4 $(M+H)^+$.

PREPARATION 34

1-[N-t-Butoxycarbonyl-3-(3-pyridyl)-(S)-alanyl]-4(R)-methylpiperidine-2(R)-carboxylic acid ethyl ester A stirred, ice-cooled suspension of N-t-butoxycarbonyl-3-(3-pyridyl)-(S)-alanine (Preparation 7; 2 g, 7.5 mmol) in dichloromethane (20 ml) was treated sequentially with 1-hydroxybenzotriazole (1.4 g, 9.1 mmol) and 1-(3-dimethylaminopropyl)-3-ethylcarbodiimide hydrochloride (2 g, 10.4 mmol). After 10 minutes, the hydrochloride salt of the title compound of Preparation 14 (1.7 g, 8.2 mmol) was added as a solution in dichloromethane (5 ml), dropwise, followed by the dropwise addition of a solution of N-methylmorpholine (0.9 g, 9 mmol) in dichloromethane (3 ml). After 72 hours at room temperature, the solvent was evaporated under reduced pressure. The residue was dissolved in ethyl acetate (50 ml) and this solution was washed successively with saturated aqueous sodium bicarbonate solution and saturated brine, dried ($MgSO_4$), filtered and evaporated under reduced pressure. The crude product was purified by chromatography on silica gel, using an elution gradient of ethyl acetate:hexane (10:90 to 100:0), to afford the title compound (2.1 g, 67%) as a hygroscopic foam. Rf 0.40 (SS 26). m/e 420.2 $(M+H)^+$.

PREPARATION 35

1-[N-t-Butoxycarbonyl-3-(1-benzyl-3-pyridinium)-(S)-alanyl]-4(R)-methylpiperidine-2(R)-carboxylic acid ethyl ester bromide To a solution of the title compound of Preparation 34 (3.3 g, 7.8 mmol) in dry ethanol (20 ml) was added a solution of benzyl bromide (2.7 g, 15.7 mmol) in dry ethanol (10 ml), dropwise, over 5 minutes at room temperature. After 18 hours the ethanol was evaporated under reduced pressure. The residue was dissolved in acetonitrile (30 ml), then the solution extracted with hexane (3×10 ml) and evaporated to dryness under reduced pressure. Solvent traces were removed azeotropically from the residue with dichloromethane to give the title compound (4.64 g, 100%) which was used without further purification.

PREPARATION 36

1-[N-t-Butoxycarbonyl-3-(1-benzyl-1,2,5,6-tetrahydro-3-pyridyl)-(S)-alanyl]-4(R)-methylpiperidine-2(R)-carboxylic acid ethyl ester Sodium borohydride (0.69 g, 18 mmol) was added in two equal portions over 5 minutes to a stirred, ice-cooled solution of the title compound of Preparation 35 (3.58 g, 6 mmol) in ethanol (40 ml). After 1 hour the solution was evaporated to dryness under reduced pressure. The residue was dissolved in dichloromethane (50 ml) and the solution washed with saturated aqueous sodium bicarbonate solution (2×15 ml) and saturated brine (15 ml), dried ($MgSO_4$), filtered and evaporated under reduced pressure. The crude product was purified by chromatography on silica gel, using an elution gradient of dichloromethane:hexane (75:25 to 100:0), followed by dichloromethane:methanol:0.880 aqueous ammonia (99:1:0.5 to 95:5:0.5), to furnish the title compound (3.18 g, 80%) as a gum. Rf 0.80 (SS 9). m/e 514.4 $(M+H)^+$.

PREPARATION 37

1-[3-(1-Benzyl-1,2,5,6-tetrahydro-3-pyridyl)-(S)-alanyl]-4(R)-methylpiperidine-2(R)-carboxylic acid ethyl ester dihydrochloride A stirred, ice-cooled solution of the title compound of Preparation 36 (3.1 g, 6 mmol) in dichloromethane (40 ml) was saturated with hydrogen chloride. After 1.5 hours the solvent and excess hydrogen chloride were removed under reduced pressure. Residual traces of hydrogen chloride were removed azeotropically from the residue with dichloromethane to afford the title compound (3 g, 100%) as a hygroscopic foam, which was used without further purification. Rf 0.42 (SS 9). m/e 414.3 $(M+H)^+$.

PREPARATION 38

4(R)-Methyl-1-[N-(2-trifluoroacetyl-1,2,3,4-tetrahydroisoquinoline-7-sulphonyl)-3-(1-benzyl-1,2,5,6-tetrahydro-3-pyridyl)-(S)-alanyl]piperidine-2(R)-carboxylic acid ethyl ester A solution of N-ethyldiisopropylamine (1.6 g, 12.4 mmol) in dichloromethane (5 ml) was added dropwise over 5 minutes to a stirred ice-cooled suspension of the title compound of Preparation 37 (1.5 g, 3 mmol) and 2-trifluoroacetyl-1,2,3,4-tetrahydroisoquinoline-7-sulfonyl chloride (Preparation 1; 1.1 g, 3.3 mmol) in dichloromethane (15 ml). After 18 hours at room temperature the solvent was evaporated under reduced pressure and the residue dissolved in ethyl acetate (50 ml). This solution was washed with water (2×10 ml), saturated aqueous sodium bicarbonate solution (2×10 ml) and saturated brine (10 ml), dried ($MgSO_4$), filtered and evaporated under reduced pressure. The residue was purified by chromatography on silica gel, using an elution gradient of ethyl acetate:hexane:diethylamine (0:100:1 to 40:60:1), to yield the title compound (1 g 48%) as a pale yellow foam. Rf 0.70 (SS 9). Found: C,58.95; H,5.83; N,7.47 $C_{35}H_{43}F_3N_4O_6S$ requires C,59.64; H,6.15; N,7.95%. m/e 705.4 $(M+H)^+$.

PREPARATION 39

4(R)-Methyl-1-[N-(2-trifluoroacetyl-1,2,3,4-tetrahydroisoquinoline-7-sulphonyl)-3-(1,2,5,6-tetrahydro-3-pyridyl)-(S)-alanyl]piperidine-2(R)-carboxylic acid ethyl ester The title compound (0.76 g, 84%) was obtained from the title compound of Preparation 38 (1 g,1.4 mmol), using the procedure of Preparation 21, as a white foam. Rf 0.25 (SS 9). Found: C,53.88; H,5.77; N,8.77. $C_{28}H_{37}F_3N_4O_6S$; 0.20 $CH_2Cl_2$ requires C,53.61; H,5.97; N,8.87%. m/e 615.4 $(M+H)^+$.

PREPARATION 40

4(R)-Methyl-1-{N-[2-trifluoroacetyl-1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}piperidine-2(R)-carboxylic acid ethyl ester The title compound (0.48 g, 47%) was obtained from the title compound of Preparation 39 (0.74 g, 1.2 mmol), using the procedure of Preparation 22, as a white foam and used without further purification. Rf 0.42 (SS 12). m/e 857.5 $(M+H)^+$.

PREPARATION 41

4(R)-Methyl-1-{N-[1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}piperidine-2(R)-carboxylic acid ethyl ester The title compound (0.43 g, 100%) was obtained from the title compound of Preparation 40 (0.47 g, 0.5 mmol), using the procedure of Preparation 23, as a white foam. Rf 0.44 (SS 9). m/e 761.5 $(M+H)^+$.

PREPARATION 42

4(R)-Methyl-1-{N-[2-methyl-1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}piperidine-2(R)-carboxylic acid ethyl ester The title compound (0.34 g, 82%) was obtained from the title compound of Preparation 41 (0.41 g, 0.5 mmol), using the procedure of Preparation 24, as a white foam. Rf 0.57 (SS 9). Found: C,58.42; H,7.67; N,9.98. $C_{38}H_{58}N_6O_9S$ requires C,58.89; H,7.54; N,10.84%. m/e 775.4 $(M+H)^+$.

PREPARATION 43

4(R)-Methyl-1-[N-(2-methyl-1,2,3,4-tetrahydroisoquinoline-7-sulphonyl)-3-(1-amidino-1,2,5,6-tetrahydro-3-pyridyl)-(S)-alanyl]piperidine-2(R)-carboxylic acid ethyl ester hydrochloride The title compound (0.18 g, 66%) was obtained from the title compound of Preparation 42 (0.33 g, 0.4 mmol), using the procedure of Preparation 25, as a white powder. Rf 0.48 (SS 27). Found: C, 52.49; H,7.18; N,12.94. $C_{28}H_{42}N_6O_5S$; HCl; $H_2O$; 0.20 $CH_2Cl_2$ requires: C,52.41; H,7.08; N, 13.00%. m/e 575.4 $(M+H)^+$.

PREPARATION 44

4-Methyl-1,2,3,6-tetrahydropyridine-2(S)-carboxylic acid methyl ester p-toluenesulphonate The title compound is obtainable via 4-methyl-1-[1-(R)-phenylethyl]-1,2,3,6-tetrahydropyridine-2(S)-carboxylic acid methyl ester by analogy with Preparation 16.

Alternatively, it may be obtained via 4-methyl-1-[1-(S)-phenylethyl]-1,2,3,6-tetrahydropyridine-2(S)-carboxylic acid methyl ester hydrochloride which is a by-product of Preparation 16, by subsequent processing as described in Preparation 16.

PREPARATION 45

4(R)-Methyl-2(S)-carboxylic acid methyl ester p-toluenesulphonate

A stirred solution of the title compound of Preparation 44 (2.0 g, 6.1 mmol) in methanol (20 ml) was hydrogenated over 10% palladium on charcoal at 414 kPa (60 p.s.i.) and room temperature for 20 hours, then the mixture filtered. The filtrate was evaporated under reduced pressure and the residue crystallised from 2-propanol to provide the title compound (1.2 g, 60%) as white crystals. Rf 0.80 (SS 28). Found: C,54.51; H,7.28; N,3.94. $C_8H_{15}NO_2$; $C_7H_8O_3S$ requires C,54.69; H,7.04; N,4.25%.

PREPARATION 46

4(S)-Methyl-2(R)-carboxylic acid methyl ester p-toluenesulphonate

The title compound (2.0 g, 77%) was obtained from the title compound of Preparation 16, using the procedure of Preparation 45, as white crystals. Rf 0.80 (SS 28). Found: C,54.44; H,7.02; N,4.60. $C_8H_{15}NO_2$; $C_7H_8O_3S$ requires C,54.69; H,7.04; N,4.25%.

PREPARATION 47

4-Methyl-1-[N-(2-trifluoroacetyl-1,2,3,4-tetrahydroisoquinoline-7-sulphonyl)-3-(1-benzyl-1,2,5,6-tetrahydro-3-pyridyl)-(S)-alanyl]-1,2,3,6-tetrahydropyridine-2(S)-carboxylic acid methyl ester The title compound (1.75 g, 82%) was obtained from the title compounds of Preparation 13 (1.82 g, 3.1 mmol) and Preparation 44 (1.1 g, 3.4 mmol), using the procedure of Preparation 20, as a white foam. Rf 0.41 (SS 9). Found: C,57.42; H,5.20; N,7.87. $C_{34}H_{39}F_3N_4O_6S$; 0.33 $CH_2Cl_2$ requires C,57.50; H,5.57; N,7.81 %. m/e 689.2 $(M+H)^+$.

PREPARATION 48

4(R)-Methyl-1-[N-(2-trifluoroacetyl-1,2,3,4-tetrahydroisoquinoline-7-sulphonyl)-3-(1-benzyl-1,2,5,6-tetrahydro-3-pyridyl)-(S)-alanyl]piperidine-2(S)-carboxylic acid methyl ester The title compound (2.09 g, 95%) was obtained from the title compounds of Preparation 13 (1.88 g, 3.19 mmol) and Preparation 45 (1.15 g, 3.49 mmol), using the procedure of Preparation 20, as a white foam. Rf 0.52 (SS 26). Found: C,58.58; H,5.81; N,7.77. $C_{34}H_{41}F_3N_4O_6S$; 0.075 $CH_2Cl_2$ requires C,58.71; H,5.95; N,8.04%. m/e 691.3 $(M+H)^+$.

PREPARATION 49

4(S)-Methyl-1-[N-(2-trifluoroacetyl-1,2,3,4-tetrahydroisoquinoline-7-sulphonyl)-3-(1-benzyl-1,2,5,6-tetrahydro-3-pyridyl)-(S)-alanyl]piperidine-2(R)-carboxylic acid methyl ester The title compound (2.3 g, 92%) was obtained from the title compounds of Preparation 13 (2.13 g, 3.6 mmol) and Preparation 46 (1.3 g, 3.9 mmol), using the procedure of Preparation 20, as a white foam. Rf 0.50 (SS 26). Found: C,58.80; H,5.89; N,7.98. $C_{34}H_{41}F_3N_4O_6S$ requires C,59.12; H,5.98; N,8.11%. m/e 691.4 $(M+H)^+$.

PREPARATION 50

4-Methyl-1-[N-trifluoroacetyl-1,2,3,4-tetrahydroisoquinoline-7-sulphonyl)-3-(1,2,5,6-tetrahydro-3-pyridyl)-(S)-alanyl]-1,2,3,6-tetrahydropyridine-2(S)-carboxylic acid methyl ester The title compound (1.24 g, 83%) was obtained from the title compound of Preparation 47 (1.72 g, 2.5 mmol), using the procedure of Preparation 21, as a white foam. Rf 0.24 (SS 9). m/e 599.2 (M+H)$^+$.

PREPARATION 51

4(R)-Methyl-1-[N-(2-trifluoroacetyl-1,2,3,4-tetrahydroisoquinoline-7-sulphonyl)-3-(1,2,5,6-tetrahydro-3-pyridyl)-(S)-alanyl]piperidine-2(S)-carboxylic acid methyl ester hydrochloride The title compound (1.47 g, 84%) was obtained from the title compound of Preparation 48 (2.0 g, 2.89 mmol), using the procedure of Preparation 21, as a pale yellow foam. Rf 0.30 (SS 9). Found: C,51.36; H,5.32; N,8.81. $C_{27}H_{35}F_3N_4O_6S$; HCl requires C,50.90; H,5.70; N,8.79%. m/e 601.3 (M+H)$^+$.

PREPARATION 52

4(S)-Methyl-1-[N-(2-trifluoroacetyl-1,2,3,4-tetrahydroisoquinoline-7-sulphonyl)-3-(1,2,5,6-tetrahydro-3-pyridyl)-(S)-alanyl]piperidine-2(R)-carboxylic acid methyl ester hydrochloride The title compound (1.79 g, 89%) was obtained from the title compound of Preparation 49 (2.3 g, 3.3 mmol), using the procedure of Preparation 21, as a pale yellow foam. Rf 0.45 (SS 9). m/e 601.3 (M+H)$^+$.

PREPARATION 53

4-Methyl-1-{N-[2-trifluoroacetyl-1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}-1,2,3,6-tetrahydropyridine-2(S)-carboxylic acid methyl ester The title compound (1.47 g, 84%) was obtained from the title compound of Preparation 50 (1.24 g, 2.1 mmol), using the procedure of Preparation 22, as a white foam. Rf 0.25 (SS 12). Found: C,53.04; H,5.79; N,9.35. $C_{38}H_{51}F_3N_6O_{10}S$; 0.33 $CH_2Cl_2$ requires C,52.96; H,5.99; N,9.66%. m/e 841.3 (M+H)$^+$.

PREPARATION 54

4(R)-Methyl-1-{N-[2-trifluoroacetyl-1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}piperidine-2(S)-carboxylic acid methyl ester The title compound (1.52 g, 75%) was obtained from the title compound of Preparation 51 (1.45 g, 2.41 mmol), using the procedure of Preparation 22, as a white foam. Rf 0.60 (SS 29)

PREPARATION 55

4(S)-Methyl-1-{N-[2-trifluoroacetyl-1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}piperidine-2(R)-carboxylic acid methyl ester The title compound (2.17 g, 88%) was obtained from the title compound of Preparation 52 (1.76 g, 2.9 mmol), using the procedure of Preparation 22, as a white foam. Rf 0.72 (SS 9).

PREPARATION 56

4-Methyl-1-{N-[1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}-1,2,3,6-tetrahydropyridine-2(S)-carboxylic acid methyl ester The title compound (1.11 g, 86%) was obtained from the title compound of Preparation 53 (1.46 g, 1.74 mmol), using the procedure of Preparation 23, as a white foam. Rf 0.43 (SS 9). m/e 745.3 (M+H)$^+$.

PREPARATION 57

4(R)-Methyl-1-{N-[1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}piperidine-2(S)-carboxylic acid methyl ester The title compound (850 mg, 64%) was obtained from the title compound of Preparation 54 (1.5 g, 1.78 mmol), using the procedure of Preparation 23, as a white foam. Rf 0.60 (SS 9). Found: C, 56.18; H,7.09; N,10.64. $C_{36}H_{54}N_6O_9S$; 0.30 $CH_2Cl_2$ requires C,56.45; H,7.13; N,10.88%.

PREPARATION 58

4(S)-Methyl-1-{N-[1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}piperidine-2(R)-carboxylic acid methyl ester The title compound (1.17 g, 61%) was obtained from the title compound of Preparation 55 (2.17 g, 2.6 mmol), using the procedure of Preparation 23, as a white foam. Rf 0.45 (SS 9). m/e 747.5.

PREPARATION 59

4-Methyl-1-{N-[2-methyl-1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}-1,2,3,6-tetrahydropyridine-2(S)-carboxylic acid methyl ester The title compound (980 mg, 86%) was obtained from the title compound of Preparation 56 (1.11 g, 1.4 mmol), using the procedure of Preparation 24, as a white foam. Rf 0.59 (SS 25). Found: C,56.21; H,7.09; N,10.19. $C_{37}H_{54}N_6O_9S$; 0.50 $CH_2Cl_2$ requires C,56.19; H,6.92; N,10.48%.

PREPARATION 60

4(R)-Methyl-1-{N-[2-methyl-1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}piperidine-2(S)-carboxylic acid methyl ester The title compound (700 mg, 83%) was obtained from the title compound of Preparation 57 (830 mg, 1.11 mmol), using the procedure of Preparation 24, as a white foam. Rf 0.61 (SS 9). Found: C,58.38; H,7.50; N,10.51. $C_{37}H_{56}N_6O_9S$ requires C,57.91; H,7.36; N,10.92. m/e 762 (M+H)$^+$.

PREPARATION 61

4(S)-Methyl-1-{N-[2-methyl-1,2,3,4-tetrahydroisoquinoline-7-sulphonyl]-3-[1-(N,N'-di-t-butoxycarbonylamidino)-1,2,5,6-tetrahydro-3-pyridyl]-(S)-alanyl}piperidine-2(R)-carboxylic acid methyl ester The title compound (1.0 g, 98%) was obtained from the title compound of Preparation 58 (1.0 g, 1.3 mmol), using the procedure of Preparation 24, as a white foam. Rf 0.48 (SS 9). Found: C,58.23; H,7.55; N,10.64. $C_{37}H_{56}N_6O_9S$ requires C,57.91; H,7.36; N,10.92%.

PREPARATION 62

4-Methyl-1-[N-(2-methyl-1,2,3,4-tetrahydroisoquinoline-7-sulphonyl)-3-(1-amidino-1,2,5,6-tetrahydro-3-pyridyl)-(S)-alanyl]-1,2,3,6-tetrahydropyridine-2(S)-carboxylic acid methyl ester hydrochloride The title compound (576 mg, 76%) was obtained from the title compound of Preparation 59 (970 mg, 1.28 mmol), using the procedure of Preparation 25, as a foam. Rf 0.41 (SS 27). Found: C,50.37; H,6.70; N,12.91. $C_{27}H_{38}N_6O_5S$; HCl; $2H_2O$; 0.25 $CH_2Cl_2$ requires C,50.16; H,6.72; N,12.88%. m/e 559.4 $(M+H)^+$.

PREPARATION 63

4(R)-Methyl-1-[N-(2-methyl-1,2,3,4-tetrahydroisoquinoline-7-sulphonyl)-3-(1-amidino-1,2,5,6-tetrahydro-3-pyridyl)-(S)-alanyl]piperidine-2(S)-carboxylic acid methyl ester hydrochloride The title compound (360 mg, 62%) was obtained from the title compound of Preparation 60 (700 mg, 0.92 mmol), using the procedure of Preparation 25, as a yellow foam. Rf 0.56 (SS 27). m/e 561.4 $(M+H)^+$.

PREPARATION 64

4(S)-Methyl-1-[N-(2-methyl-1,2,3,4-tetrahydroisoquinoline-7-sulphonyl)-3-(1-amidino-1,2,5,6-tetrahydro-3-pyridyl)-(S)-alanyl]piperidine-2(R)-carboxylic acid methyl ester dihydrochloride The title compound (810 mg, 98%) was obtained from the title compound of Preparation 61 (1.0 g, 1.3 mmol), using the procedure of Preparation 25, as a white foam. Rf 0.48 (SS 27). Found: C,51.40; H,6.97; N,13.55. $C_{27}H_{40}N_6O_5S$; 2HCl requires C,51.18; H,6.68; N,13.20%.

Biological activity

The following Table illustrates the in vitro inhibitory activities against thrombin and trypsin for two of the compounds of the invention.

TABLE

| EXAMPLE | ki(M) THROMBIN | TRYPSIN |
|---|---|---|
| 5 | $1.9 \times 10^{-9}$ | $2.4 \times 10^{-6}$ |
| 6 | $9.9 \times 10^{-9}$ | $6.9 \times 10^{-7}$ |

Safety profile

Certain compounds of the invention have been tested at multiple doses of up to 30 mg/kg i.v. in mouse and up to 100 mg/kg i.v. in rat without showing any sign of adverse toxicity.

I claim:

1. A compound of formula (I):

or a pharmaceutically acceptable salt thereof, or a pharmaceutically acceptable solvate of either entity,
wherein Y is optionally monounsaturated $C_3$–$C_5$ alkylene optionally substituted with $C_1$–$C_4$ alkyl or methylene;

$R^1$ is H; $C_1$–$C_4$ alkyl optionally substituted with $C_1$–$C_4$ alkoxy, OH, $NR^5R^6$, $CONR^5R^6$, $C_3$–$C_6$ cycloalkyl or aryl; or $C_3$–$C_6$ alkenyl;

$R^2$ is H; $C_1$–$C_4$ alkyl optionally substituted with $C_1$–$C_4$ alkoxy, OH, $NR^5R^6$, $CONR^5R^6$, $C_3$–$C_6$ cycloalkyl or aryl; or $CONR^5R^6$;

$R^3$ and $R^4$ are each independently selected from H; $C_1$–$C_4$ alkyl optionally substituted with $NR^5R^6$; $C_1$–$C_4$ alkoxy; halo; $CONR^5R^6$ and aryl;

aryl is phenyl optionally substituted with one, two or three substituents independently selected from $C_1$–$C_4$ alkyl, $C_1$–$C_4$ alkoxy, OH, halo and $CF_3$;

$R^5$ and $R^6$ are each independently selected from H and $C_1$–$C_4$ alkyl; and m and n are each independently 1, 2 or 3.

2. A compound according to claim 1 wherein the preferred stereoisomer is of formula (IA):

3. A compound according to claim 2 wherein Y is optionally monounsaturated $C_4$ alkylene substituted with methyl or ethyl; $R^1$ is $C_1$–$C_4$ alkyl; $R^2$ is H; $R^3$ and $R^4$ are H; and m and n are each independently 1 or 2.

4. A compound according to claim 3 of formula (IB):

wherein — represents an optional carbon-carbon single bond; $R^1$ and $R^7$ are methyl; m is 1 or 2; and n is 2.

5. A compound according to claim 4 wherein the compound of formula (IB) is selected from 4-methyl-1-[N-(2-methyl-1,2,3,4-tetrahydroisoquinoline-7-sulphonyl)-3-(1-amidino-1,2,5,6-tetrahydro-3-pyridyl)-(S)-alanyl]-1,2,3,6-tetrahydropyridine-2(R)-carboxylic acid;

4-methyl-1-[N-(3-methyl-2,3,4,5-tetrahydro-1H-3-benzazepine-7-sulphonyl)-3-(1-amidino-1,2,5,6-tetrahydro-3-pyridyl)-(S)-alanyl]-1,2,3,6-tetrahydropyridine-2(R)-carboxylic acid; and 4(R)-methyl-1-[N-(2-methyl-1,2,3,4-tetrahydroisoquinoline-7-sulphonyl)-3-(1-amidino-1,2,5,6-tetrahydro-3-pyridyl)-(S)-alanyl]piperidine-2(R)-carboxylic acid;

and pharmaceutically acceptable salts thereof, and pharmaceutically acceptable solvates of either entity.

6. A pharmaceutical composition comprising a compound of claim 1, a pharmaceutically acceptable salt thereof or a pharmaceutically acceptable solvate of said compound or said salt, and a pharmaceutically acceptable carrier or diluent.

7. A compound of formula (II): t.0770 wherein Y is optionally monounsaturated $C_3$–$C_5$ alkylene optionally substituted with $C_1$–$C_4$ alkyl or methylene;

$R^1$ is H; $C_1$–$C_4$ alkyl optionally substituted with $C_1$–$C_4$ alkoxy, OH, $NR^5R^6$, $CONR^5R^6$, $C_3$–$C_6$ cycloalkyl or aryl; or $C_3$–$C_6$ alkenyl;

$R^2$ is H; $C_1$–$C_4$ alkyl optionally substituted with $C_1$–$C_4$ alkoxy, OH, $NR^5R_6$, CONR5$R^6$, $C_3$–$C_6$ cycloalkyl or aryl; or $CONR^5R^6$;

$R^3$ and $R^4$ are each independently selected from H; $C_1$–$C_4$ alkyl optionally substituted with $NR^5R^6$; $C_1$–$C_4$ alkoxy; halo; $CONR^5R^6$ and aryl;

aryl is phenyl optionally substituted with one, two or three substituents independently selected from $C_1$–$C_4$ alkyl, $C_1$–$C_4$ alkoxy, OH, halo and $CF_3$;

$R^5$ and $R^6$ are each independently selected form H and $C_1$–$C_4$ alkyl; m and n are each independently 1, 2 or 3; and $R^8$ is $C_1$–$C_3$ alkyl.

8. A compound according to claim 7 wherein $R^8$ is methyl or ethyl.

9. A method of treating a mammal to cure or prevent deep vein thrombosis (DVT) after surgery, major medical illness, paralysis, malignancy, prolonged immobilization trauma, application of lower limb plaster casts, or fractures of the lower limbs or pelvis; recurrent DVT; DVT during pregnancy when there is a previous history thereof; reocclusion following thrombolytic therapy; chronic arterial obstruction; peripheral vascular disease; acute myocardial infarction; unstable angina; atrial fibrillation; thrombotic stroke; transient ischaemic attacks; disseminated intravascular coagulation; coagulation in extra-corporeal circuits; occlusion of arterio-venous shunts and blood vessel grafts (including coronary artery by-pass grafts); restenosis and occlusion following angioplasty; neurodegenerative disorders; inflammatory disorders; or scarring; which comprises administering to said mammal an effective amount of a compound of claim 1, a pharmaceutically acceptable salt thereof, or a pharmaceutically acceptable solvate of said compound or said salt or a pharmaceutical composition containing any of the foregoing.

10. A process for the preparation of a compound of formula (I):

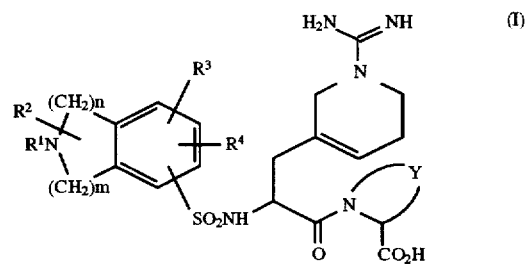

or a pharmaceutically acceptable salt thereof, or a pharmaceutically acceptable solvate of either entity, wherein Y is optionally monounsaturated $C_3$–$C_5$ alkylene optionally substituted with $C_1$–$C_4$ alkyl or methylene;

$R^1$ is H; $C_1$–$C_4$ alkyl optionally substituted with $C_1$–$C_4$ alkoxy, OH, $NR^5R^6$, $CONR^5R^6$, $C_3$–$C_6$ cycloalkyl or aryl; or $C_3$–$C_6$ alkenyl;

$R^2$ is H; $C_1$–$C_4$ alkyl optionally substituted with $C_1$–$C_4$ alkoxy, OH, $NR^5R^6$, $CONR^5R^6$, $C_3$–$C_6$ cycloalkyl or aryl; or $CONR^5R^6$;

$R^3$ and $R^4$ are each independently selected from H; $C_1$–$C_4$ alkyl optionally substituted with $NR^5R^6$; $C_1$–$C_4$ alkoxy; halo; $CONR^5R^6$ and aryl;

aryl is phenyl optionally substituted with one, two or three substituents independently selected from $C_1$–$C_4$ alkyl, $C_1$–$C_4$ alkoxy, OH, halo and $CF_3$;

$R^5$ and $R^6$ are each independently selected from H and $C_1$–$C_4$ alkyl; and m and n are each independently 1, 2 or 3;

which comprises acid- or base-catalysed hydrolysis of a compound of formula (II):

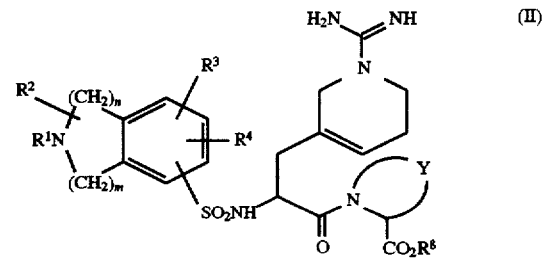

wherein $R^8$ is $C_1$–$C_3$ alkyl, and Y, $R^1$, $R^2$, $R^3$, $R^4$, m and n are as previously defined in this claim;

followed by optional formation of a pharmaceutically acceptable salt of the required product or a pharmaceutically acceptable solvate of either entity.

11. A process according to claim 10 which is base-catalysed in aqueous medium, optionally in the presence of a cosolvent, at from about 0° C. to about 100° C.

12. A process according to claim 11 wherein the base is an alkali metal hydroxide.

13. A process according to claim 12 wherein the base is sodium hydroxide and the reaction is conducted at from about 0° C. to about room temperature.

14. A process according to claim 13 wherein $R^8$ is methyl or ethyl.

15. A process according to claim 14 wherein the preferred stereoisomer of a compound of formula (I) produced form the corresponding stereoisomer of a compound of formula (II) is of formula (IA):

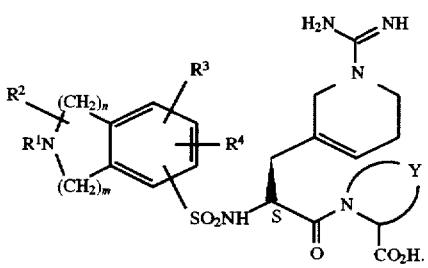

16. A process according to claim 15 where Y is optionally monounsaturated $C_4$ alkylene substituted with methyl or ethyl; $R^1$ is $C_1$–$C_4$ alkyl; $R^2$ is H; $R^3$ and $R^4$ are H; and m and n are each independently 1 or 2.

17. A process according to claim 16 wherein the compound produced is of formula (IB):

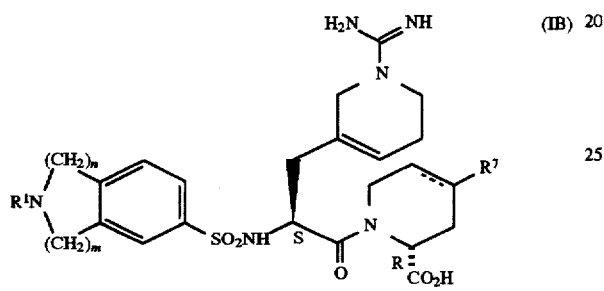

wherein — represents an optional carbon-carbon single bond; $R^1$ and $R^7$ are methyl; m is 1 or 2; and n is 2.

18. A process according to claim 17 wherein the compound of formula (IB) produced is selected from 4-methyl-1-[N-(2-methyl-1,2,3,4-tetrahydroisoquinoline-7-sulphonyl)-3-(1-amidino-1,2,5,6-tetrahydro-3-pyridyl)-(S)-alanyl]-1,2,3,6-tetrahydropyridine-2(R)-carboxylic acid;

4-methyl-1-[N-(3-methyl-2,3,4,5-tetrahydro-1H-3-benzazepine-7-sulphonyl)-3-(1-amidino-1,2,5,6-tetrahydro-3-pyridyl)-(S)-alanyl]-1,2,3,6-tetrahydropyridine-2(R)-carboxylic acid; and 4(R)-methyl-1-[N-(2-methyl-1,2,3,4-tetrahydroisoquinoline-7-sulphonyl)-3-(1-amidino-1,2,5,6-tetrahydro-3-pyridyl)-(S)-alanyl]piperidine-2(R)-carboxylic acid;

and pharmaceutically acceptable salts thereof, and pharmaceutically acceptable solvates of either entity.

\* \* \* \* \*